(12) United States Patent
Genco et al.

(10) Patent No.: US 11,419,901 B2
(45) Date of Patent: Aug. 23, 2022

(54) ***PORPHYROMONAS GINGIVALIS* IMMUNE MODULATORS AND USES THEREOF**

(71) Applicant: Trustees of Tufts College, Boston, MA (US)

(72) Inventors: Caroline Attaro Genco, Newton, MA (US); George Papadopoulos, Boston, MA (US)

(73) Assignee: Trustees of Tufts College, Boston, MA (US)

( * ) Notice: Subject to any disclaimer, the term of this patent is extended or adjusted under 35 U.S.C. 154(b) by 0 days.

(21) Appl. No.: 16/964,577

(22) PCT Filed: Jan. 23, 2019

(86) PCT No.: PCT/US2019/014836
§ 371 (c)(1),
(2) Date: Jul. 23, 2020

(87) PCT Pub. No.: WO2019/147731
PCT Pub. Date: Aug. 1, 2019

(65) Prior Publication Data
US 2020/0390827 A1    Dec. 17, 2020

Related U.S. Application Data

(60) Provisional application No. 62/621,024, filed on Jan. 23, 2018.

(51) Int. Cl.
*A61K 35/74*  (2015.01)
*A61P 37/02*  (2006.01)
*A61P 35/00*  (2006.01)
*A61K 39/00*  (2006.01)
*A61K 39/39*  (2006.01)

(52) U.S. Cl.
CPC .......... *A61K 35/74* (2013.01); *A61K 39/0008* (2013.01); *A61K 39/0011* (2013.01); *A61K 39/39* (2013.01); *A61P 35/00* (2018.01); *A61P 37/02* (2018.01)

(58) Field of Classification Search
None
See application file for complete search history.

(56) References Cited

U.S. PATENT DOCUMENTS 7,622,128 B2    11/2009   Darveau et al.
8,802,419 B2     8/2014   Lien et al.

FOREIGN PATENT DOCUMENTS

WO    WO 97/34629 A1    9/1997

OTHER PUBLICATIONS

Slocum, Connie, et al. "Distinct lipid a moieties contribute to pathogen-induced site-specific vascular inflammation." PLoS Pathog 10.7 (2014): e1004215.
Genco, Caroline; Abstract "P. Gingivalis Mediated Evasion Strategies," NIH Grant No. R01DE023501-01 through R01DE023501-05; Funding date May 5, 2013 to Apr. 1, 2016.
International Search Report issued in PCT/US2019/014836 dated May 7, 2019.

*Primary Examiner* — Brian Gangle
(74) *Attorney, Agent, or Firm* — Morse, Barnes-Brown & Pendleton, P.C.; Lisa M. Warren, Esq.; Erin E. Bryan, Esq.

(57) ABSTRACT

A heat killed *Porphyromonas gingivalis* bacterium expressing a homogenous lipid A structure having a molecular negative mass ion of 1368, 1435/1449, or 1690/1768 is used as an immunomodulator. The immunomodulator may be used in combination with an antigen of interest to potentiate or restrain a host immune response toward the selected antigen.

30 Claims, 27 Drawing Sheets

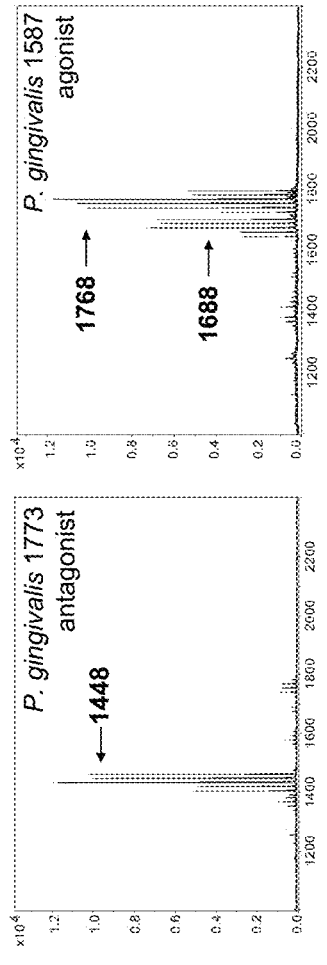
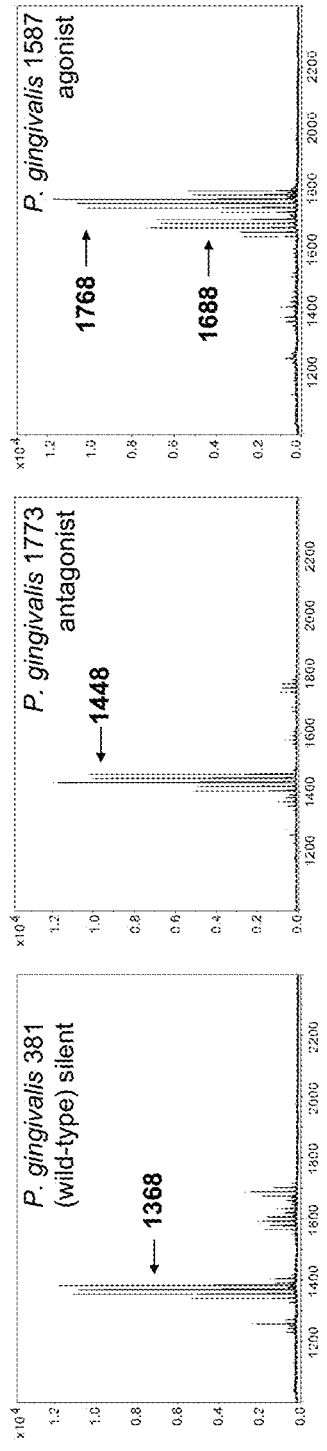
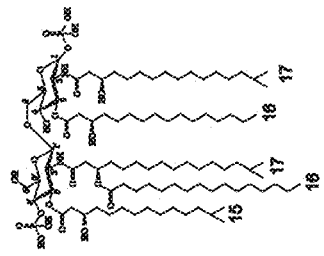
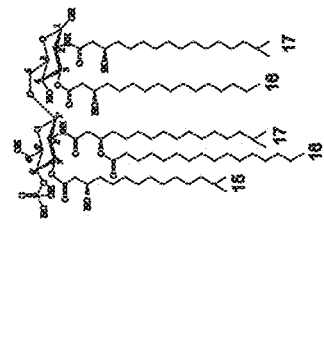
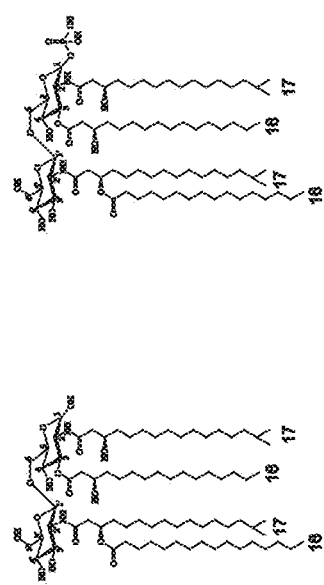
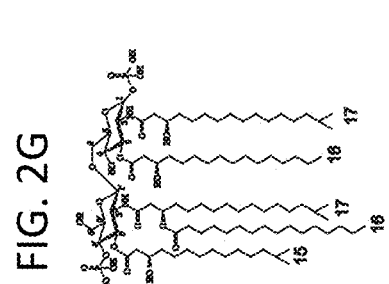

| Strain | Genotype | Major lipid A species | Molecular weight (m/z) | TLR4 activity |
|---|---|---|---|---|
| P. gingivalis 381 (WT) | wild-type | Tetra-acylated, non-phosphorylated | 1368 | Silent |
| P. gingivalis 1773 (Antagonist) | 1-phosphatase KO (PG1773) | Tetra-acylated, mono-phosphorylated (1-phosphate) | 1448 | Antagonist |
| P. gingivalis 1587 (Agonist) | 4'-phosphatase KO (PG1587) | Penta-acylated, mono- and di-phosphorylated | 1688, 1768 | Agonist |

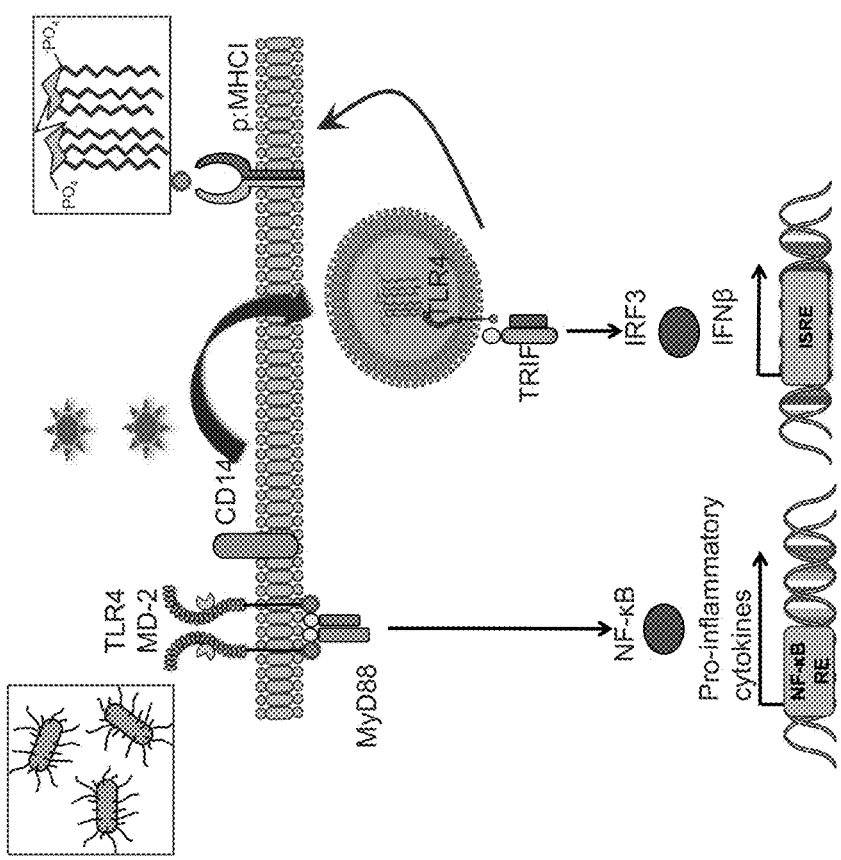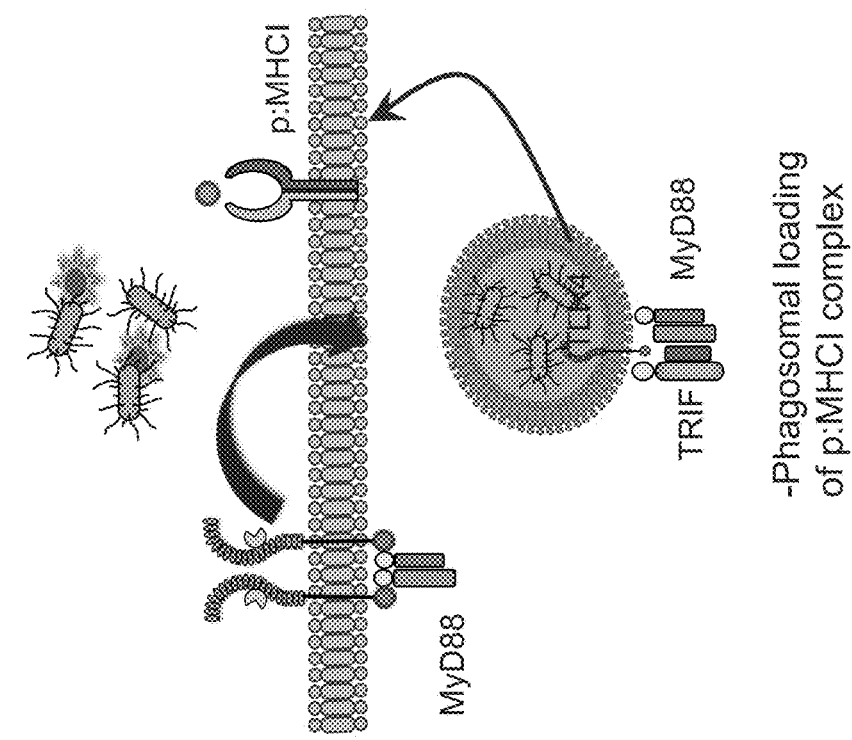
FIG. 3

TLR4 signaling and antigen presentation

- DCs are key antigen presenting cells
  - Bridge innate and adaptive immunity
- Cross-presentation
  - Presentation of foreign antigens on MHC-I
  - Important for anti-microbial & anti-tumor immunity, as well as maintenance of T cell tolerance to self
  - Developmentally regulated during maturation
- TLR4 engagement
  - Initiates developmental process of maturation, when DCs become compotent to present antigen and induce tolerance or immunity.
  - Activities regulated during maturation:
    - Antigen uptake is decreased
      - Degradation is slowed down.
      - Cross-presentation
      - Expression of co-stimulatory molecules

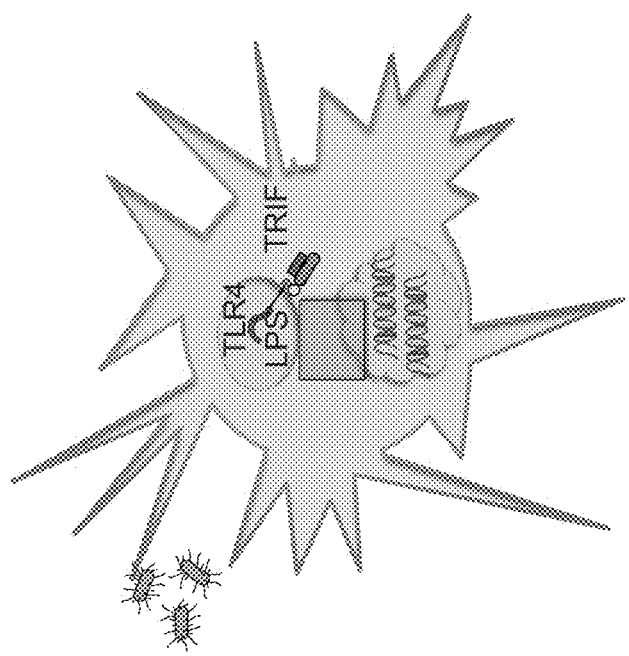

FIG. 4

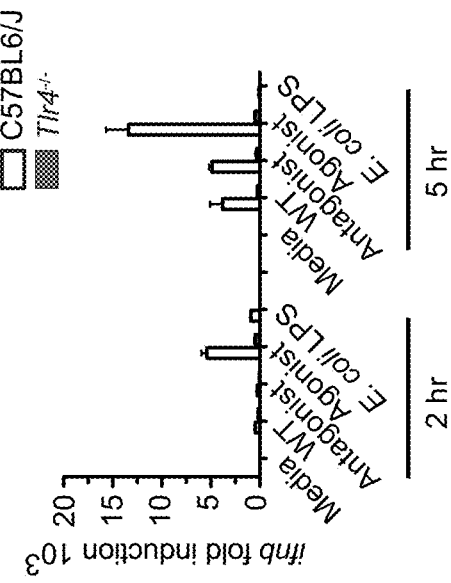
FIG. 6B
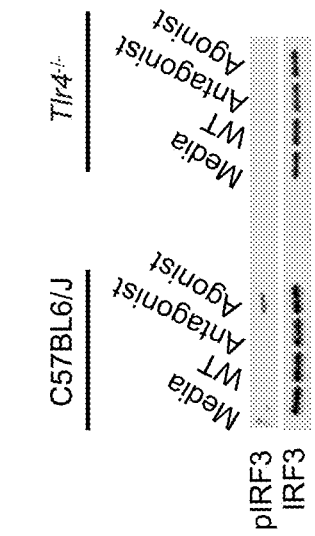
FIG. 6D
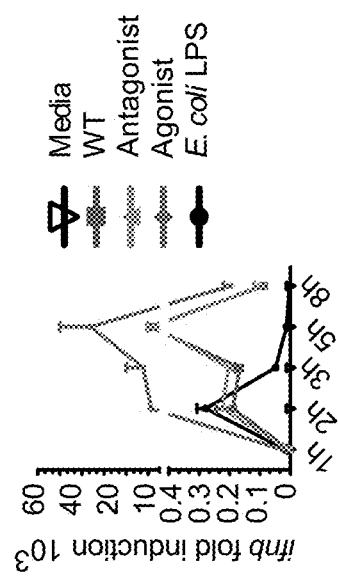
FIG. 6A
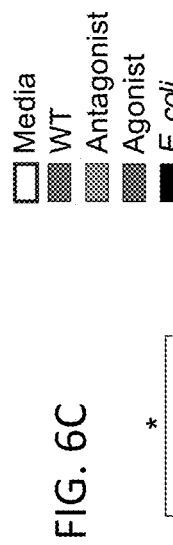
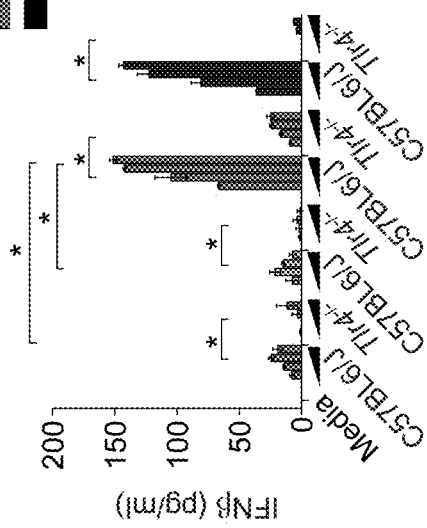
FIG. 6C

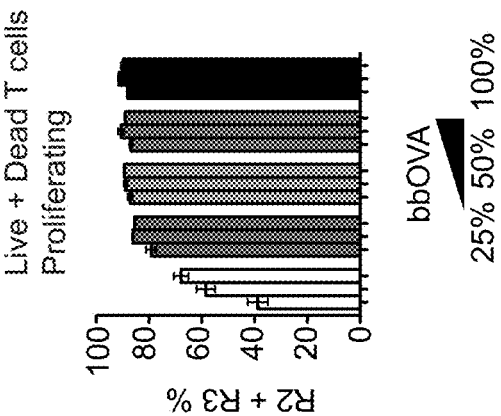
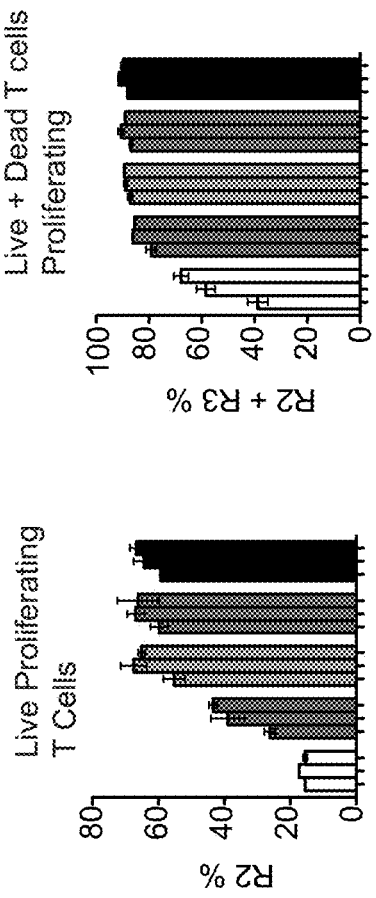
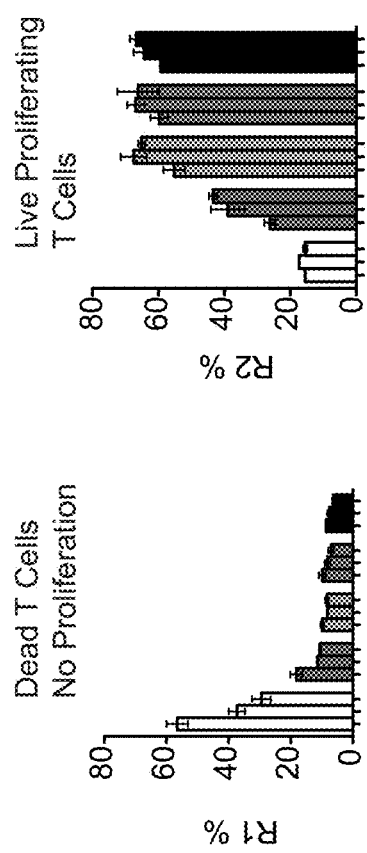
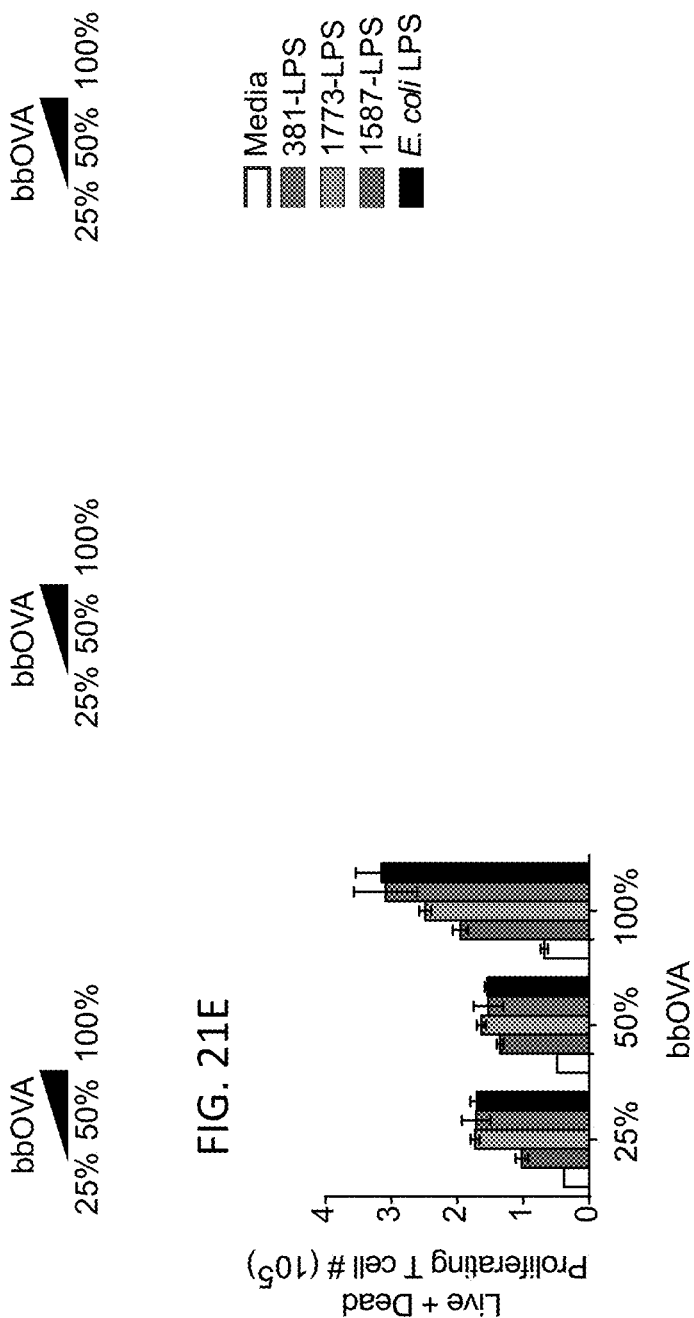

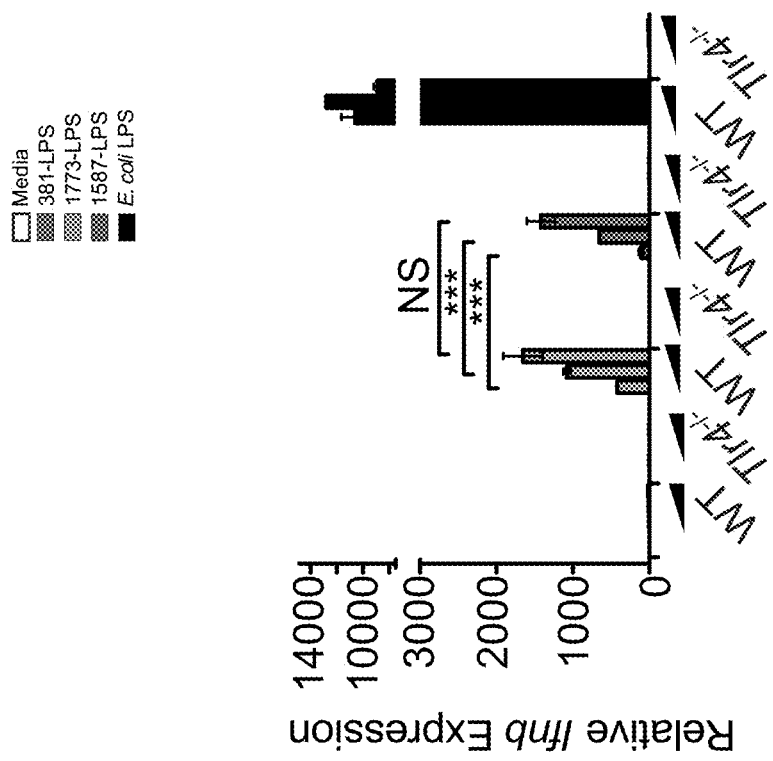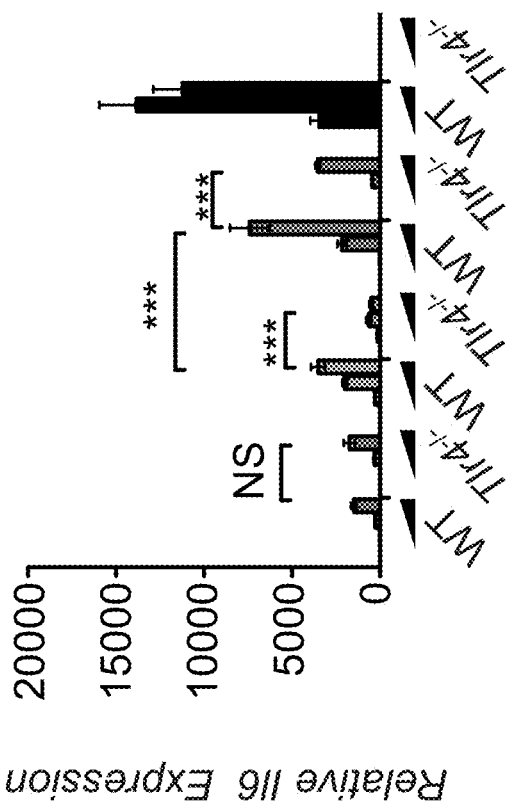
FIG. 24

PORPHYROMONAS GINGIVALIS IMMUNE MODULATORS AND USES THEREOF

RELATED APPLICATIONS

This application is a national stage filing under 35 U.S.C. 371 of International Application No. PCT/US2019/014836, filed Jan. 23, 2019, which claims the benefit of U.S. Provisional Application No. 62/621,024, filed on Jan. 23, 2018. The entire teachings of the above application are incorporated herein by reference. International Application No. PCT/US2019/014836 was published under PCT Article(2) in English.

GOVERNMENT SUPPORT

This invention was made with government support under R01DE023501 awarded by the National Institutes of Health. The government has certain rights in the invention.

BACKGROUND OF THE INVENTION

Cancer remains a major source of morbidity and mortality, with 17.5 million cases and 8.5 million deaths worldwide in 2015 [40]. For nearly 3 decades, cancer research has focused on identifying the genetic mutations that are responsible for driving malignant cell behavior. As such, anti-cancer treatments have emphasized targeting either the proliferation of cancer cells or the specific molecular basis driving their growth (e.g., cytotoxic chemotherapy, radiation therapy, and molecular targeted therapy). However, the recent success of immunotherapy in the treatment of melanoma and non-small-cell lung cancer, two tumor types that are traditionally recalcitrant to traditional forms of therapy, has provided direct clinical proof that cancer can be treated through the modulation of immunity [41, 42]. Immunotherapy development currently tends to focus broadly on three treatment categories: chimeric antigen receptor (CAR) T-cell therapies, vaccines, and checkpoint blockade strategies [43]. Tumor types such as melanoma, which exhibit a high immune infiltrate, are those that are most responsive to immunotherapy. Most solid tumors however, exemplified by breast cancer, exhibit a relative paucity of nearby T cells, which limits the potential of immunotherapy [2, 5, 44].

Diseases caused by dysregulated immune activation, including autoimmune syndromes and allergy, remain a major health challenge. Autoimmune disease is estimated to afflict between 5% and 7% of the population in the developed world [80], while in the United States alone an estimated 60 million people suffer from allergies at a cost of about $20 billion per year [7]. Although there have been recent advances in treatment, notably the development of anti-TNF biologics, therapies to date induce non-specific immunosuppression resulting in potentially severe side effects [4]. A major advance in treatment of autoimmune syndromes would be the development of antigen-specific immune therapies, i.e., strategies to induce immune tolerance [6]. To date, perhaps the most well-studied examples of tolerance have been in transplantation [81]. Although the phenomenon of tolerance was first described in 1953 by Medawar and colleagues [82], induction of tolerance in the clinic has been challenging. Recent approaches such as costimulatory molecule blockade have failed to result in lasting graft survival [83] and are now used as alternative forms of immunosuppression but are limited by cost and complications associated with suppression of immunity. Tolerance remains a major goal in transplantation, autoimmunity, and inflammation because it has the potential to prevent unwanted immune responses without side effects while maintaining immunological memory to pathogen responses.

The ability to tune the nature and magnitude of antigen-specific immune responses has the potential for broad therapeutic impact in the treatment of multiple immune-mediated diseases, ranging from cancer to autoimmunity and transplant rejection. Recent advances in the understanding of immune regulation have led to the hope that through appropriate manipulation of the immune system it will be possible to treat disorders ranging from autoimmune diseases that result from dysregulated immune activation, to cancer, whose elimination by induction of tumor-specific immune responses seems achievable. Immune-mediated diseases represent a major health problem with ~250,000 to 400,000 new cases annually in the United States resulting in annual costs of $100 billion [7]. Dysregulation of immune responses that result in either immune activation or immune suppression is at the core of many of these diseases. Hyper activation of self-antigen- or microbial antigen-specific effector T and B cells, together with defects in the regulatory arm of the adaptive immune system, results in the breakdown of immune homeostasis and development of a wide array of inflammatory diseases. Immune suppression is a key component of cancer survival in the face of immune surveillance. Efforts to combat cancer through activation of tumor-specific immunity have shown some promise, particularly in a subset of cancers [3, 8]. However, significant challenges remain, particularly in the treatment of solid tumors [2, 3, 5]. Recent advances in the understanding of immune regulation have resulted in the development of several immune-based therapies that suppress tissue inflammation in autoimmune disorders, yet none of these are able to specifically target disease specific processes [4, 6]. As a result, all have potentially severe side effects such as infection and cancer. Thus, there is an urgent need for improved approaches that target modulation of the immune response. In particular, development of tools to precisely modulate antigen-specific responses, either to promote or suppress them, is essential.

SUMMARY OF THE INVENTION

The use of *Porphyromonas gingivalis* bacterium strains expressing defined lipid A moieties and/or select preparations of lipopolysaccharide obtained from these strains as immune system modulators is described herein. The immunomodulators may be used in combination with an antigen of interest to potentiate or restrain the host immune response toward the selected antigen.

In some aspects, the disclosure provides pharmaceutical compositions comprising a heat killed *Porphyromonas gingivalis* bacterium expressing a homogenous lipid A structure, e.g., having a molecular negative mass ion of 1368, 1435/1449, or 1690/1768; and a pharmaceutically acceptable carrier.

In some embodiments of any aspect described herein, the composition further includes an antigen. The *P. gingivalis* bacterium may express the antigen. Alternatively, the antigen may be absorbed to the *P. gingivalis* bacterium. In some embodiments, the antigen is selected from the group consisting of a tumor antigen, a bacterial antigen, a viral antigen, infectious disease antigens, and self-antigens.

In some embodiments, the composition further includes an adjuvant. The adjuvant may be selected from the group consisting of alum, incomplete Freund's adjuvant, montanide, GM-CSF, imiquimod, resiquimod, and a saponin.

In some embodiments, the composition is administered to a patient for treatment of cancer, infectious disease, or autoimmunity.

In some aspects, the disclosure provides an immunomodulatory agent comprising a heat killed *Porphyromonas gingivalis* bacterium expressing a homogenous lipid A structure having a molecular negative mass ion of 1368, 1435/1449, or 1690/1768.

In some aspects, the disclosure provides a pharmaceutical composition comprising a heat killed purified *P. gingivalis* lipopolysaccharide (LPS) where a lipid portion of LPS has a molecular negative mass ion of 1368 or 1690/1768; and a pharmaceutically acceptable carrier.

In some aspects, the disclosure provides methods for stimulating an immune response in a subject. The methods comprise administering a composition comprising a heat killed *Porphyromonas gingivalis* bacterium expressing a homogenous lipid A structure having a molecular negative mass ion of 1368, 1435/1449, or 1690/1768 and an antigen, wherein the composition promotes an immune response to the antigen.

In some embodiments, the composition elicits a T cell response to the antigen. In some embodiments, the composition is administered for treatment of a tumor. In some embodiments, the composition is administered for treatment of cancer. In some embodiments, the antigen is a tumor antigen or an infectious disease antigen. In some embodiments, the composition comprises at least two different antigens. In some embodiments, the composition includes an adjuvant.

In some aspects, the disclosure provides methods for stimulating an immune response in a subject. The methods comprise administering a composition comprising a heat killed *Porphyromonas gingivalis* bacterium expressing a homogenous lipid A structure having a molecular negative mass ion of 1368, 1435/1449, or 1690/1768 and an antigen, wherein the composition inhibits an immune response to the antigen.

In some embodiments, the inhibition of an immune response comprises inducing tolerance to the antigen or suppressing an immune response to the antigen. In some embodiments, the composition induces dendritic cells to express immune-regulatory modulators (e.g., co-inhibitor ligands or immune suppressive cytokines). In some embodiments, the composition is administered for treatment of an autoimmune disease or disorder, treatment of an allergy, or treatment of graft versus host disease.

In some embodiments, the antigen is a self-antigen. In some embodiments, the composition comprises an adjuvant.

In some aspects, the disclosure provides methods of stimulating an immune response against a tumor in a subject. The methods comprise administering to the subject a composition comprising a heat killed *Porphyromonas gingivalis* bacterium expressing a homogenous lipid A structure having a molecular negative mass ion of 1368, 1435/1449, or 1690/1768 and a tumor antigen from the tumor, in an amount sufficient to elicit an immune response against the tumor in the subject.

In some aspects, the disclosure provides methods for suppressing an immune response against a self-antigen in a subject suffering from an autoimmune disease. The methods comprise administering to the subject a composition comprising a heat killed *Porphyromonas gingivalis* bacterium expressing a homogenous lipid A structure having a molecular negative mass ion of 1368, 1435/1449, or 1690/1768 and a self-antigen, in an amount sufficient to suppress the immune response against the self-antigen.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual*, 3' ed., Cold Spring Harbor Laboratory Press. Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics. 11th Ed., McGraw Hill, 2005, Katzung, B. (ed.) Basic and Clinical Pharmacology, McGraw-Hill/Appleton & Lange; $10^{th}$ ed. (2006) or 11th edition (July 2009). Non-limiting information regarding genes and genetic disorders is found in McKusick, V. A.; Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, available on the World Wide Web at ncbi.nlm.nih.gov/omim/ and in Online Mendelian Inheritance in Animals (OMIA), a database of genes, inherited disorders and traits in animal species (other than human and mouse), at omia.angis.org.au/contact.shtml.

All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The above discussed, and many other features and attendant advantages of the present inventions will become better understood by reference to the following detailed description of the invention.

BRIEF DESCRIPTION OF THE DRAWINGS

FIGS. 2A-2I demonstrate that *P. gingivalis* strain 381 utilizes endogenous lipid A 1- and 4-phosphatase activities to modify lipid A structure and modulate TLR4 signaling. FIGS. 2A-2C depict MALDI-TOF MS analysis of lipid A isolated from *P. gingivalis* wild-type strain 381 (FIG. 2A) or the lipid A phosphatase mutant strains *P. gingivalis* 1773 (FIG. 2B) and *P. gingivalis* 1587 (FIG. 2C). Arrows indicate the major lipid A structure expressed by each strain. FIGS. 2D-2G depict the four major lipid A structures produced by *P. gingivalis*, which have been previously characterized (43). FIG. 2H contains information regarding genotype, lipid A expression, and immunological activity of the *P. gingivalis* strains described herein. FIG. 2I depicts TLR4 activation by *P. gingivalis* wild-type and lipid A mutant strains. *E. coli* was used as control to indicate maximal stimulation. HEK293 cells expressing human CD14, TLR4/MD-2, and an NF-kB inducible secreted embryonic alkaline phosphatase (SEAP) reporter gene were stimulated with graded doses of intact bacteria for 16 hr. SEAP activity in culture supernatants was determined using a fluorescence based assay. Values are reported as relative fluorescence units (RFU). Data represent the mean±SD of triplicate samples from one representative of three independent experiments.

FIG. 3 demonstrates that TLR4 signaling can be broadly divided into two distinct downstream pathways. The first is the MyD88-dependent pathway that is initiated at the plasma membrane and elicits robust pro-inflammatory cytokine production. The second pathway is initiated by the signaling adapter TRIF after TLR4 is delivered to intracellular compartments and induces the production of type I interferons. The TRIF-dependent pathway does not induce robust pro-inflammatory responses but is critical for immunogenicity (development of adaptive immune responses). Both TRIF and type I IFN are crucial for the adjuvant activity of TLR4 agonists in vivo. The figure illustrates two strategies for potentiating antigen-presentation via TLR engagement. The first involves physical association of the microbial vector or TLR ligand and the antigen of interest (as in FIGS. 5-14). The second strategy involves administering the microbial vector or TLR ligand and the antigen of interest at separate times (as in FIG. 15-24).

FIG. 4 shows TLR4 signaling and antigen presentation in dendritic cells.

FIGS. 6A-6D demonstrate that *P. gingivalis* strains expressing immunologically silent or antagonistic lipid A structures evade TRIF-dependent signaling. FIG. 6A depicts the kinetics of ifnh mRNA induction in DCs treated with *P. gingivalis* strains (MOI 25) for 1, 2, 3, 5, and 8 hr. *E. coli* LPS (100 ng/ml) was used as a positive control. Relative lfnb mRNA expression was measured by qPCR. Results are expressed as fold change over media control. Data represent the mean±SD of duplicate cultures from one representative of three independent experiments. FIG. 6B shows that *P. gingivalis*-induced ifnb expression is TLR4-dependent at both early and late time points. C57BL6/J and Tlr4$^{-/-}$ DCs were treated with *P. gingivalis* strains (MOI 10) or *E. coli* LPS (100 ng/ml) for 2 or 5 hr. Relative ifnb mRNA expression was measured by qPCR. Results are expressed as fold change over media control. Data show the mean±SD of triplicate cultures. FIG. 6C demonstrates that secretion of IFNβ by DCs treated with *P. gingivalis* strains is TLR4-dependent. C57BL6/J and Tlr4$^{-/-}$ DCs were treated with increasing doses (MOI 10, 25, 50, and 100) of *P. gingivalis* strains or *E. coli* for 18 hr. Levels of IFNβ in culture supernatants were measured by ELISA. FIG. 6D depicts Western blot analysis of total and phosphorylated IRF3 in whole cell lysates from WT and Tlr4$^{-/-}$ DCs treated or not with *P. gingivalis* strains (MOI 10) for 60 min.

FIG. 9A depicts histogram overlays comparing OVA staining among *P. gingivalis* strains. FIG. 9B shows light scattering properties of OVA-coated *P. gingivalis* strains. Results show that *P. gingivalis* strains were evenly coated with OVA protein.

FIGS. 21A-2E demonstrate that immunologically silent LPS expressed by *P. gingivalis* wild-type promotes T cell tolerance (cross-tolerance). DCs treated with LPS from *P. gingivalis* or *E. coli* (100 ng/ml; 16-18 hr) or media alone were pulsed with bbOVA for 1 hr and co-cultured with CTV labeled OT-I cells. T cell proliferation and viability were assessed by flow cytometry after 72 hr. FIG. 21A depicts representative scatter plots for CTV dilution versus Live Dead staining. Three gated regions are shown: dead T cells that did not proliferate (RI), live proliferating T cells (R2), and T cells that underwent activation induced cell death i.e. tolerized T cells (R3). Bar graphs show the percentage of cells in R1 (FIG. 21B), R2 (FIG. 21C), and R2+R3 (FIG. 21D). The absolute numbers of live and dead T cells that underwent proliferation (R2+R3) are shown in (FIG. 21E). Data represent the mean±SD of triplicate samples from one representative of three independent experiments.

FIG. 24 depicts expression of MyD88 and TRIF dependent genes in DCs stimulated with purified *P. gingivalis* LPS. WT and Tlr4$^{-/-}$ DCs were treated with *P. gingivalis* LPS or *E. coli* LPS at a concentration of 10, 100, or 1000 ng/ml for 2 h. Relative expression of the MyD88-dependent gene 116 and the TRIF-dependent gene ifnb were measured by qPCR. Results are expressed as fold change over media control. Data represent the mean±SD of triplicate cultures from one representative of three independent experiments. *p<0.05; p<0.01; *p<0.001; NS, not significant; Two-way ANOVA with Bonferroni's post-test. Note that both agonist and antagonist LPS species induce TRIF-dependent gene expression and promote cross-priming.

DETAILED DESCRIPTION OF THE INVENTION

Figure 1:
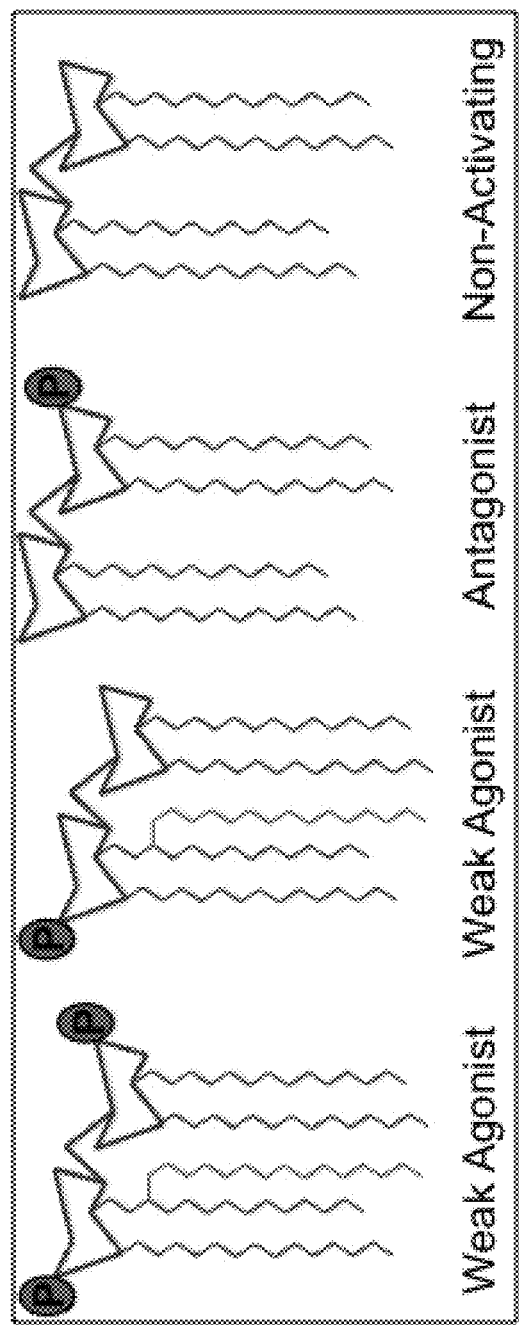
FIG. 1 provides a schematic of *P. gingivalis* lipid A structures. Expression of the specific lipid A moieties is dependent on growth conditions. Shown in red are the phosphate groups and fatty acid chains that can be removed by bacterial phosphatase and deacylase activities as discussed in the text.

New therapies that target specific immune responses are vitally needed for treatment of an array of immune-mediated disorders. Microbial vectors may be used to modulate antigen-specific adaptive immune responses for therapeutic purposes. The microbial vectors can be engineered to express a multitude of antigens and extended to treat a variety of immune-mediated diseases. The ability to tune the nature and magnitude of antigen-specific immune responses has the potential for broad therapeutic impact in the treatment of multiple immune-mediated diseases. Genetically modified strains of a common host-adapted pathogen (e.g., *Porphyromonas gingivalis*) are used to manipulate the immune system for therapeutic potential. Strains of the pathogen expressing defined lipid A moieties in combination with an antigen of interest can be used as therapeutic tools to potentiate or restrain T cell responses for the treatment of inflammatory diseases.

Described herein are agents, compositions, and methods for modulating an immune response of a subject using genetically modified strains of the bacterium *Porphyromonas gingivalis* (*P. gingivalis*). The *P. gingivalis* bacterium may be viable or inactivated, and expresses a homogenous lipid A structure. In some aspects, the lipid A structure has a molecular negative mass ion of 1368, 1435/1449, or 1690/1768. These structures correspond to tetra-acylated non-phosphorylated lipid A, tetra-acylated mono-phosphorylated lipid A, and mono- or di-phosphorylated penta-acylated lipid A. The lipid A structure having a molecular negative mass ion of 1368, 1435/1449, or 1690/1768 may include mimetics and derivatives thereof. By derivative is meant a compound that is structurally similar and possesses similar immunomodulating properties as the native compound. A derivative or mimetic may be a naturally occurring compound or prepared synthetically. The *P. gingivalis* bacterium described herein is used as an immunomodulator.

In some embodiments, the genetically modified bacterium is a *P. gingivalis* lipopolysaccharide (LPS). The *P. gingivalis* LPS may be a *P. gingivalis* LPS where a lipid portion of LPS has a molecular negative mass ion of 1368 or 1690/1768. In some aspects, the LPS having a molecular negative mass ion of 1368 or 1690/1768 includes derivatives and mimetics thereof.

In some aspects, the *P. gingivalis* bacterium is a heat killed bacterium. For example, broth grown cultures of *P. gingivalis* may be washed one to five times in PBS and re-suspended at ~$10^9$ CFU/mL. Bacteria may then be heat killed at between 50 to 75 degrees Celsius for 5 to 15 minutes. In certain aspects, broth grown cultures of *P.* gingivalis are washed three times in PBS and re-suspended at ~$10^9$ CFU/mL. Bacteria are then heat killed at 65 degrees Celsius for 10 minutes. The time and temperature for heat killing can vary depending on density and volume of the liquid culture. Additional methods for heat killing a bacterium are well known in the art, such as those described in Miyamoto, "Pathogen-Accelerated Atherosclerosis Occurs Early after Exposure and Can Be Prevented via Immunization. Infection and Immunity" (2006), and such method are incorporated herein.

In certain embodiments, the *P. gingivalis* bacterium is a heat killed *P. gingivalis* bacterium expressing a lipid A structure (e.g., a homogenous lipid A structure) having a molecular negative mass ion of 1368, 1435/1449, or 1690/1768. In other embodiments, the *P. gingivalis* bacterium is a heat killed *P. gingivalis* LPS where a lipid portion of LPS has a molecular negative mass ion of 1368 or 1690/1768.

A live or heat killed intact *P. gingivalis* bacterium may have various benefits as compared to a purified *P. gingivalis* LPS. For example, whole bacteria may induce dendritic cell maturation as assessed by the upregulation of co-stimulatory molecules and MHC complexes that promote T cell activation. In addition, it has been demonstrated that particulate antigens (i.e., whole bacteria) induce a stronger cytotoxic T cell response when compared to soluble antigens.

In some embodiments, the genetically modified *P. gingivalis* bacterium is combined or used in combination with an antigen. In some aspects, the bacterium is engineered to express the antigen. In other aspects, the antigen is physically connected to the bacterium, e.g., adsorbed to the bacterium through a variety of covalent or non-covalent interactions. In still other aspects, the bacterium and antigen are administered to a subject independently. The antigen may be one or more antigens targeted for a therapeutic response or purpose. In some aspects, the antigen is selected from the group consisting of a tumor antigen, a bacterial antigen, a viral antigen, an infectious disease antigen, a self-antigen, an autoimmune antigen, an MHC antigen, and combinations thereof.

A pharmaceutical composition comprising an immunomodulator (e.g., a heat killed *P. gingivalis* bacterium) may include additional agents. In some aspects, the composition includes an adjuvant. Any adjuvant that stimulates a desired response in a subject when administered may be selected. For example, the adjuvant may be selected from the group consisting of alum, incomplete Freund's adjuvant, montanide, GM-CSF, imiquimod, resiquimod, a saponin, any other acceptable adjuvants which are capable of eliciting a desired immune response, and combinations thereof.

As disclosed herein, pharmaceutical compositions include a *P. gingivalis* bacterium (e.g., a heat killed *P. gingivalis* bacterium) and one or more pharmaceutically acceptable carriers. Suitable carriers will depend on the condition being treated along with the route of administration. It will be understood that the pharmaceutical compositions described herein may be used as adjuvants to increase an immune response to an antigen or enhance certain activities of cells of the immune system, or in some instances as a prophylactic or therapeutic composition to prevent or treat a particular condition in a subject.

The *P. gingivalis* bacterium described herein is present in a pharmaceutical composition in an amount effective to modulate an immune response, which is the amount of bacterium required to achieve the desired effect in terms of stimulating, inhibiting or directing a desired immune response, or treating or inhibiting a disease or condition. The pharmaceutical compositions can also act as an adjuvant when co-administered with an antigen.

Compositions may be formulated for direct administration of the active compounds (e.g., the *P. gingivalis* bacterium) to subjects without dilution, either in conjunction with a selected antigen, e.g., as a vaccine, or other active agent, or alone. Alternatively, the compositions may be formulated as more concentrated compositions of the compounds for later dilution, so as to avoid shipment and/or storage of large amounts of diluent (e.g. water, saline or aqueous materials). In some aspects, pharmaceutical compositions of this invention intended for direct or immediate administration to a subject (e.g., without dilution) will contain one or more of the compounds, in a therapeutically effective amount. This amount will vary based on the particular *P. gingivalis* bacterium and on the therapeutic (or prophylactic) effect desired.

For pharmaceutical compositions including a *P. gingivalis* bacterium as described herein and a pharmaceutically acceptable carrier, the pharmaceutically acceptable carrier can be one or more compatible solid or liquid vehicles, fillers, diluents, or encapsulating substances which are suitable for administration to a human or non-human animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically-acceptable carriers should be of sufficiently high purity and sufficiently low toxicity to render them suitable for administration to the human or non-human animal being treated.

Some examples of substances which can serve as pharmaceutically-acceptable carriers are pyrogen-free water; isotonic saline, phosphate buffer solutions; sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof in certain embodiments. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that a compound can be provided as a pharmaceutically acceptable pro-drug, or an active metabolite can be used.

The pharmaceutical composition may be administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical composition may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

In some embodiments, the pharmaceutical composition is administered to a subject to modulate an immune response in the subject. In some aspects, the composition is used in combination with an antigen of interest to potentiate or restrain the host immune response toward the selected antigen. In some aspects, the immune response is potentiated or activated. In other aspects, the immune response is restrained. The effect of the composition is dependent based on the antigen added to the composition. In some embodiments, the composition is combined with an antigen of interest, or is administered to a subject separately from the antigen, to stimulate or otherwise modulate the desired immune response. In some aspects, the composition is administered to a subject or a patient for treatment of a cancer, an infectious disease, or an autoimmunity.

The compositions of the present invention exhibit strong immunomodulating effects when administered over a wide range of dosages and a wide range of ratios. The amount of the immunomodulatory composition (e.g., the composition comprising the heat killed *P. gingivalis* bacterium) administered is generally selected as an amount which induces an immunoprotective response without significant adverse side effects. Such amount will also vary depending upon which specific immunomodulators and immunogens are employed and how they are presented. Generally, it is expected that each dose will comprise about 1-1000 µg of antigen and 1-100 µg of immunomodulator, most typically about 2-100 µg of antigen and 150 µg of immunomodulator, and preferably about 5-50 µg of antigen preparation and 1-25 µg of immunomodulator. Of course, the dosages administered may be dependent upon the age, weight, kind of concurrent treatment, if any, and nature of the antigen and immunomodulator being administered.

In some embodiments, methods for modulating an immune response in a subject are provided. The methods for modulating an immune response in a subject may include administering a genetically modified *P. gingivalis* bacterium or compositions comprising a genetically modified *P. gingivalis* bacterium. In some aspects, the administered bacterium is a *P. gingivalis* bacterium expressing a homogenous lipid A structure having a molecular negative mass ion of 1368, 1435/1449, or 1690/1768. In certain aspects, the *P. gingivalis* bacterium is a heat killed bacterium. In other aspects, the administered genetically modified *P. gingivalis* bacterium is a heat killed *P. gingivalis* LPS where a lipid portion of LPS has a molecular negative mass ion of 1368 or 1690/1768.

In some aspects, the methods for modulating an immune response include administering a composition including the genetically modified *P. gingivalis* bacterium and an antigen. In other aspects, the antigen is administered to the subject separately from the composition including the genetically modified *P. gingivalis* bacterium. The composition administered to the subject may further include an adjuvant as described herein.

In certain aspects, the methods include stimulating an immune response in a subject by administering a composition comprising a genetically modified *P. gingivalis* bacterium and an antigen, where the composition promotes an immune response to the antigen. The composition may elicit a T cell response to the antigen. In certain aspects, the antigen is a tumor antigen. Cancer cells often have distinctive antigens on their surfaces, such as truncated epidermal growth factor, folate binding protein, epithelial mucins, melanoferrin, carcinoembryonic antigen (CEA), prostate-specific membrane antigen (PSMA), HER2-neu, and others. Tumor antigens may include all potentially antigenic molecules. In some aspects, the composition is administered to the subject for treatment of a tumor. The composition may be administered to treat a cancer in the subject. In certain aspects, the cancer is a prostate, colon, breast, ovarian, pancreatic, brain, head and neck, melanoma, leukemia, lymphoma, or some other cancer exhibiting a tumor antigen.

In some aspects, a microbial-derived tumor antigen or a tumor antigen is comprised of natural or synthetic amino acids, e.g., in the form of peptides, polypeptides, or proteins, polysaccharides, fats, nucleotides (including RNA and DNA) or can be mixtures thereof, covalent or not. In some embodiments, antigens can be isolated from natural sources, synthesized by means of solid phase synthesis, or can be obtained by way of recombinant DNA techniques.

In other aspects, the composition is administered for treatment of an infectious disease and the antigen is an infectious disease antigen or a viral antigen. A viral antigen may be derived from an influenza virus, feline leukemia virus, feline immunodeficiency virus, HIV-1, HIV-2, herpes simplex virus type 2, cytomegalovirus, hepatitis A, B, C or E, respiratory syncytial virus, human papilloma virus, rabies, measles, or hoof and mouth disease viruses. Vaccine antigens can also be derived from bacterial or protozoan sources, such as anthrax, diphtheria, Lyme disease, malaria, *M. tuberculosis. S. pneumoniae, H. influenza*, Leishmaniasis, *T. cruzi*, Ehrlichia, or Candida.

In other embodiments, the methods include stimulating an immune response in a subject by administering a composition comprising a genetically modified *P. gingivalis* bacterium and an antigen, where the composition inhibits an immune response to the antigen. In certain aspects, the antigen is a self-antigen (e.g., is not a foreign antigen). In some embodiments, the composition is administered to a subject to induce tolerance to the antigen. In other embodiments, the composition is administered to a subject to suppress an immune response to the antigen. The composition may induce dendritic cells (DCs) to express immune-regulatory modulators (e.g., co-inhibitor ligands or immune suppressive cytokines). The composition may be administered to treat an autoimmune disease or disorder, an allergy, asthma, or graft-versus-host disease in a subject. Examples of an autoimmune disease include type 1 diabetes, conventional organ-specific autoimmune diseases, neurological diseases, rheumatic diseases, psoriasis, connective tissue diseases, autoimmune cytopenias, and other autoimmune diseases. Such conventional organ specific autoimmunity may include thyroiditis (Graves+Hashimoto's), gastritis, adrenalitis (Addison's), ovaritis, primary biliary cirrhosis, myasthenia gravis, gonadal failure, hypoparathyroidism, alopecia, malabsorption syndrome, pernicious anemia, hepatitis, anti-receptor antibody diseases and vitiligo. Such neurological diseases may include schizophrenia, Alzheimer's disease, depression, hypopituitarism, diabetes insipidus, sicca syndrome and multiple sclerosis. Such rheumatic diseases/connective tissue diseases may include rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris, Sjogren's syndrome. Other autoimmune related diseases may include autoimmune uvoretinitis, glomerulonephritis, post myocardial infarction cardiotomy syndrome, pulmonary hemosiderosis, amyloidosis, sarcoidosis, aphthous stomatitis, and other immune related diseases. In other embodiments the composition can be used with one or more selected MHC antigens of the tissue graft to prevent transplant rejection in a host, e.g., to inhibit or treat graft-versus-host disease.

In some aspects, the heat killed *P. gingivalis* bacterium is administered alone, i.e., without a co-administered antigen, to potentiate the immune system for treatment of chronic infectious diseases, especially in immune compromised patients. Illustrative examples of infectious diseases for which this approach may be employed for therapeutic or prophylactic treatment can be found in U.S. Pat. No. 5,508,310, incorporated in its entirety by reference. Potentiation of the immune system in this way can also be useful as a preventative measure to limit the risks of other infections, such as, e.g., nosocomial and/or post-surgery infections.

In some embodiments, the immunomodulator is used in combination with an antigen for in vitro or ex vivo vaccination, including stimulating dendritic cells, B cells, T cells, and other immune effectors.

While any suitable carrier known to those of ordinary skill in the art may be employed in the pharmaceutical compositions described herein, the type of carrier will typically vary depending on the desired mode of intended administration. The compositions may be formulated for any appropriate manner of administration, including for example, topical, inhalational, oral, nasal, intravenous, intraperitoneal, intradermal, intratumoral, subcutaneous, intramuscular administration, or by other means known by those skilled in the art.

In some embodiments, pharmaceutical compositions may be administered directly to a tissue, e.g., a tissue in which cancer cells are found or one in which a cancer is likely to arise. Direct tissue administration may be achieved by direct injection. The composition may be administered once, or alternatively may be administered in a plurality of administrations. If administered multiple times, the composition may be administered via different routes. For example, the first (or the first few) administrations may be made directly into the affected tissue while later administrations may be systemic.

For oral administration, compositions can be formulated readily by combining the active agent(s) with pharmaceutically acceptable carriers well known in the art. Such carriers enable the agents to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol, cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In certain embodiments, the composition is provided as a biocompatible microparticle or implant that is suitable for implantation into a mammalian recipient. Exemplary bioerodible implants that are useful in accordance with this method are described in PCT International Application Publication No. WO 95/24929, entitled "Polymeric Gene Delivery System", which reports on a biodegradable polymeric matrix for containing a biological macromolecule. The polymeric matrix may be used to achieve sustained release of the agent in a subject. In some embodiments, an agent described herein may be encapsulated or dispersed within a biocompatible, preferably biodegradable polymeric matrix. The polymeric matrix may be in the form of a microparticle such as a microsphere (wherein the agent is dispersed throughout a solid polymeric matrix) or a microcapsule (wherein the agent is stored in the core of a polymeric shell). Other forms of polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Other delivery systems can include time-release, delayed release or sustained release delivery systems. Such systems can avoid repeated administrations of the composition, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active agent for at least 30 days, and preferably 60 days. Long-term sustained release implants are well-known to those of ordinary skill in the art and include some of the release systems described above.

In some embodiments, it may be advantageous to formulate oral or parenteral compositions in dosage unit form for ease of administration and uniformity of dosage. Unit dosage form as used herein refers to physically discrete units suited as unitary dosages for the subject to be treated; each unit containing a predetermined quantity of active compound calculated to produce the desired therapeutic effect in association with the required pharmaceutical carrier.

In some aspects, a vaccine formulation is administered to the mucosae, in particular to the oral cavity, and preferably to a sublingual site, for eliciting an immune response. Oral cavity administration provides a means for eliciting mucosal immunity, which can often be difficult to achieve with traditional parenteral delivery, and which can provide protection from airborne pathogens and/or allergens.

The heat killed *P. gingivalis* bacterium can be employed as the sole immunomodulator, or alternatively, can be administered together with other immunomodulators or immunoeffectors. For example, such immunomodulators can include oil-based adjuvants (for example, Freund's Complete and Incomplete), liposomes, mineral salts (for example, AlK(SO4)2, AlNa(SO4)2, AlNH4 (SO4), silica, alum, Al(OH)3, Ca3(PO4)2, kaolin and carbon), polynucleotides (for example, poly IC and poly AU acids), polymers (for example, non-ionic block polymers, polyphosphazenes, cyanoacrylates, polymerase-(DL-lactide-co-glycoside), among others, and certain natural substances (wax D from *M. tuberculosis*, as well as substances found in *C. parvum, B. pertussis*, and members of the genus *Brucella*), bovine serum albumin, diphtheria toxoid, tetanus toxoid, edestin, keyhole-limpet hemocyanin, and eukaryotic proteins such as interferons, interleukins, or tumor necrosis factor. Such proteins may be obtained from natural or recombinant sources according to methods known to those skilled in the art. When obtained from recombinant sources, the immunomodulator may comprise a protein fragment comprising at least the immunostimulatory portion of the molecule. Other known immunostimulatory macromolecules which can be used include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenylmethane-3,3'-dicarboxylic acid and 4-nitro-2-aminobenzoic acid (See Sela, Science 166:1365-1374 (1969)) or glycolipids, lipids or carbohydrates.

The following examples are intended to illustrate but not limit the invention.

EXAMPLES

Background

Recent advances in the understanding of immune regulation have led to the hope that through appropriate manipulation of the immune system it will be possible to treat disorders ranging from autoimmune diseases that result from dysregulated immune activation [4, 6, 7], to cancer, whose elimination by elicitation of an appropriate immune response seems achievable [2, 3, 5, 8]. A majority of efforts currently underway for the development of immune-modulatory therapies have focused on targeting specific components of the host immune response, including pattern recognition receptors (PRRs) [9]. PRRs, including Toll-like receptors (TLRs), detect conserved microbial products and play a central role in the activation of innate and adaptive immune responses to infection. Several host-adapted bacteria express structurally divergent forms of lipid A as a strategy to evade innate immune detection at TLR4, and recent studies suggest that it may be possible to manipulate these microbes for therapeutic purposes [10-15].

The utility of engineered strains of a host-adapted oral pathogen for the treatment of cancer and transplant rejection will be tested. Microbial vectors can be modified to express a multitude of antigens and tailored for patient specific responses. This approach has the potential to overcomes issues with general systemic immune activation and suppression and to limit off target side effects of these interventions. For example, recombinant microbial vectors expressing defined lipid A moieties and an antigen of interest can be harnessed for use as therapeutic vaccines for the treatment of a broad array of diseases including infectious diseases, cancer, and autoimmunity.

Harnessing Microbes to Manipulate Innate and Adaptive Responses:

Pattern recognition receptors (PRRs), including Toll-like receptors (TLRs), detect conserved microbial products and play a central role in the activation of innate and adaptive immune responses to infection. As a result, microbes have evolved mechanisms to evade or manipulate recognition by PRRs. The immune response during Gram-negative bacterial infection is initiated following recognition of lipopolysaccharide (LPS) by the PRR TLR4, which signals through the adaptor proteins MyD88 and TRIF. Lipid A is the primary immunologically active moiety of LPS. The canonical lipid A species of Escherichia coli is a hexa-acylated and di-phosphorylated structure that potently stimulates TLR4 [14]. However, several Gram-negative bacteria synthesize LPS with non-canonical lipid A structures to evade or manipulate host immune responses [14, 15]. Because of its potent immune-stimulatory activity. LPS has been considered of potential use as an adjuvant. However, because of its toxicity, it is has been necessary to develop modified, less toxic forms [10, 11, 16]. One such form, monophosphoryl lipid A, derived from Salmonella minnesota, is approved for clinical use as a vaccine adjuvant [10, 12]. However, given the wide range of naturally occurring lipid A structures and their correspondingly wide range of immunological activities, the use of differently modified lipid A for immune modulation has not been exhausted [13, 14]. Soluble LPS directly activates multiple cell types to induce antigen-non-specific responses. Significantly, LPS on the surface of Gram-negative bacteria exhibits specificity in the induction of antigen-specific TLR4-dependent T cell responses to bacterial antigens via activation of dendritic cells (DCs) to process and present bacterial antigens to naïve T cells.

Critical Role of Antigen-Presenting Cells (APCs) in Activation of Specific Adaptive Responses:

DCs are uniquely equipped to activate naïve T cells for development of antigen-specific immune responses. They process peptides derived from extracellular sources and present them on major histocompatibility complex (MHC) II to prime naïve CD4 T cells. They can also present extracellular antigens on MHC-I to CD8 T cells (cross-presentation) to prime a cytotoxic CD8 T cell (CTL) response (cross-priming) [17, 18]. In addition to priming T cell responses. DCs can induce T cell tolerance or promote iTreg differentiation [19]. Cross-presentation of self-antigens is important for induction of peripheral CD8 T cell tolerance (cross-tolerance) [20]. Immature DCs sense pathogens and danger molecules through PRRs, including TLR4, resulting in a process of maturation characterized by up regulation of costimulatory molecules, along with antigen processing, presentation, and cross-presentation and the production of cytokines that direct T cell polarization [21]. Recent studies using microbial strains engineered to express distinct lipid A species (FIG. 1) revealed unexpected effects of these strains on DC function that suggest their utility for therapeutic manipulation of the immune system, to either stimulate or suppress adaptive immune responses.

The Host-Adapted Pathogen P. gingivalis Expresses Different Lipid a Moieties that Induce Distinct Immunomodulatory Activity:

P. gingivalis a Gram-negative bacterium that colonizes the oral mucosa and is associated with periodontal disease [22, 23], although it can also be present in healthy individuals [24, 25]. P. gingivalis employs immune evasive mechanisms that prevent its elimination by the immune system [26, 27]. Prominent among P. gingivalis immune-modulatory strategies is the production of heterogeneous lipid A species [28, 29]. P. gingivalis intrinsically expresses several underacylated lipid A moieties (penta or tetra) that, compared to canonical lipid A structures, are poorly recognized by TLR4 (FIG. 1) [28, 30].

When grown under hemin-deplete conditions, P. gingivalis expresses lipid A 1- and 4'-phosphatases to produce a non-phosphorylated, tetra-acylated lipid A that does not activate TLR4 signaling and mono- and di-phosphorylated, penta-acylated lipid A species that have weak TLR4 activity (FIG. 1). When grown under hemin-replete conditions, the 1-phosphatase is suppressed, resulting in expression of a mono-phosphorylated, tetra-acylated lipid A species that functions as a TLR4 antagonist (FIG. 1) [28]. P. gingivalis mutant strains that lack either 1- or 4'-phosphatase were constructed [I]. A mutant lacking 4'-phosphatase ($1587_{381}$) produces a di-phosphorylated, penta-acylated lipid A with TLR4 agonist activity that induces robust NF-κB-dependent proinflammatory cytokines and inflammasome activation in macrophages [1]. A deletion mutant lacking 1-phosphatase ($1773_{381}$) produces a mono-phosphorylated, tetra-acylated lipid A with TLR4 antagonistic activity and induces low levels of inflammatory cytokines. P. gingivalis wild-type strain (381) expresses a mixture of agonist, non-activating, and antagonist lipid A and behaves like the antagonist strain, consistent with a dominant effect of the antagonist species.

Figures 2H, 2I:
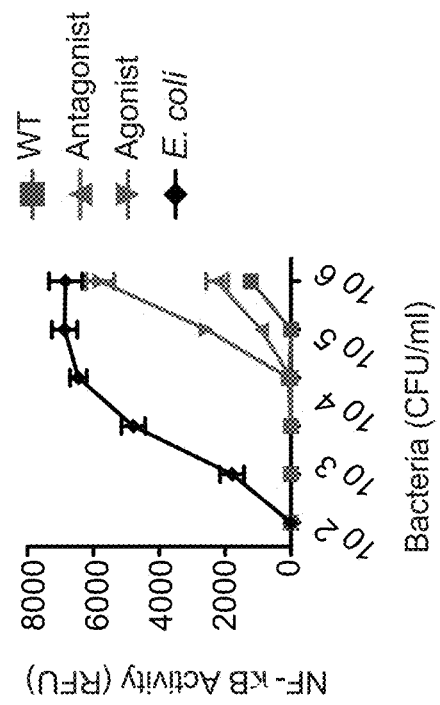

Harnessing Bacterial Mutants to Modulate Antigen-Specific CD4 and/or CD8 T Cell Responses:

It was demonstrated that *P. gingivalis* induces up regulation of costimulatory molecules (CD80, CD86, CD40, and MHCI and II) on bone marrow-derived DCs (BMDCs), independent of the lipid A species expressed (data not shown). Thus, the agonist and antagonist strains have the potential to promote priming of naïve T cells. All strains also induced DCs to secrete pro-inflammatory cytokines, although the agonist strain induced slightly higher levels (FIG. 2). In TLR4BMDCs, cytokine induction was reduced, indicating the contribution of TLR4 signaling (FIG. 2). Although the agonist and wild-type strains were capable of signaling through TLR4 on DCs, only the agonist strain induced IFNβ via a TLR4-dependent mechanism (FIG. 6). Unlike TLR4-driven expression of pro-inflammatory cytokines, which is primarily the result of TLR4 signaling from the cell surface using the adaptor MyD88, induction of IFNβ by TLR4 requires TLR4 internalization and endosomal signaling using the adaptor TRIF. All strains induced equivalent internalization of TLR4 (data not shown) indicating that failure of wild type and antagonist strains to induce IFNβ occurs downstream of this event.

While up regulation of costimulatory molecules and secretion of cytokines is necessary for DC priming of T cell responses, it is not sufficient, as DCs must process and present antigen to prime T cell responses. The ability of *P. gingivalis* agonist and antagonist strains coated with OVA to drive cross priming of OVA-specific OT-I CD8 cells by BMDCs was tested. Significantly, T cell proliferation was only observed with antigen presented by DCs treated with the agonist strain (FIG. 11).

Figure 10:
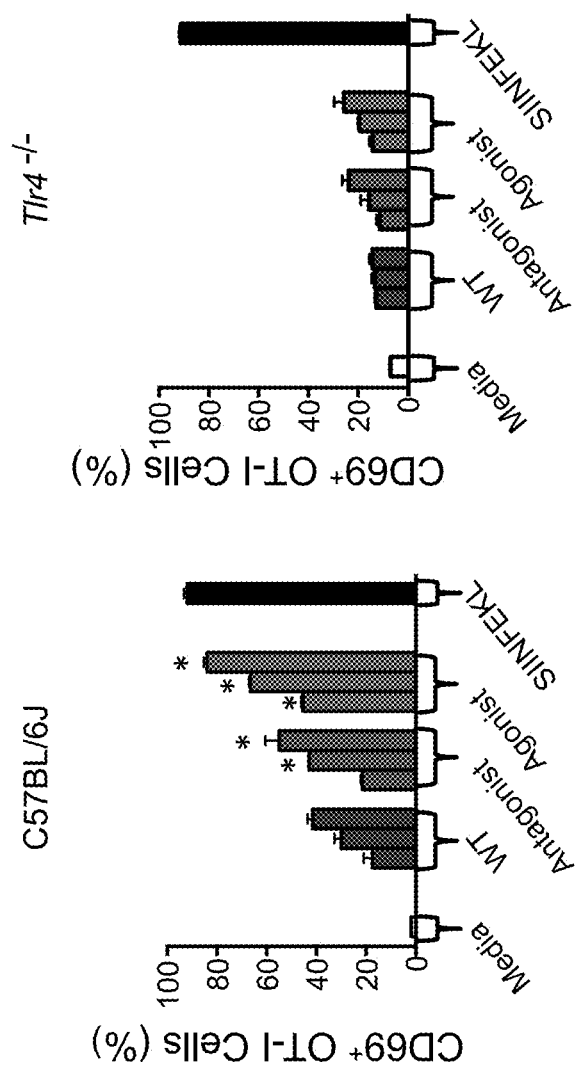
FIG. 10 shows that TLR4 engagement by *P. gingivalis* strains expressing divergent lipid A structures promotes cross-presentation of microbial antigens by DCs. C57BL6/J and Tlr4$^{-/-}$DCs were pulsed with increasing doses of OVA-coated *P. gingivalis* strains (MOI 10, 25, or 50) for 3-5 hr and then co-cultured with TCR transgenic CD8$^+$ OT-I T cells, which recognize the SIINFEKL (SEQ ID NO: 1) peptide from OVA presented by the H-2K$^b$ MHC-I molecule. Cross-presentation was assessed by upregulation of CD69 on OT-I T cells after 18 hr. Treatment of C57BL6/J DCs with each strain led to a dose-dependent increase in the efficiency of cross-presentation. This increase was dependent on TLR4, as cross-presentation was severely impaired in Tlr4$^{-/-}$DCs and did not with higher bacterial doses. The pre-processed SIINFEKL (SEQ ID NO: 1) peptide (0.01 ng/ml) was used as a control and was presented with equal efficiency by C57BL6/J and Tlr4$^{-/-}$DCs. These results demonstrate that all *P. gingivalis* strains engage TLR4 and promote cross-presentation of microbe-associated antigens. Thus, bacteria expressing defined lipid A moieties are suitable vectors for antigen delivery and potentiation of antigen-specific immune responses.
Figure 11A:
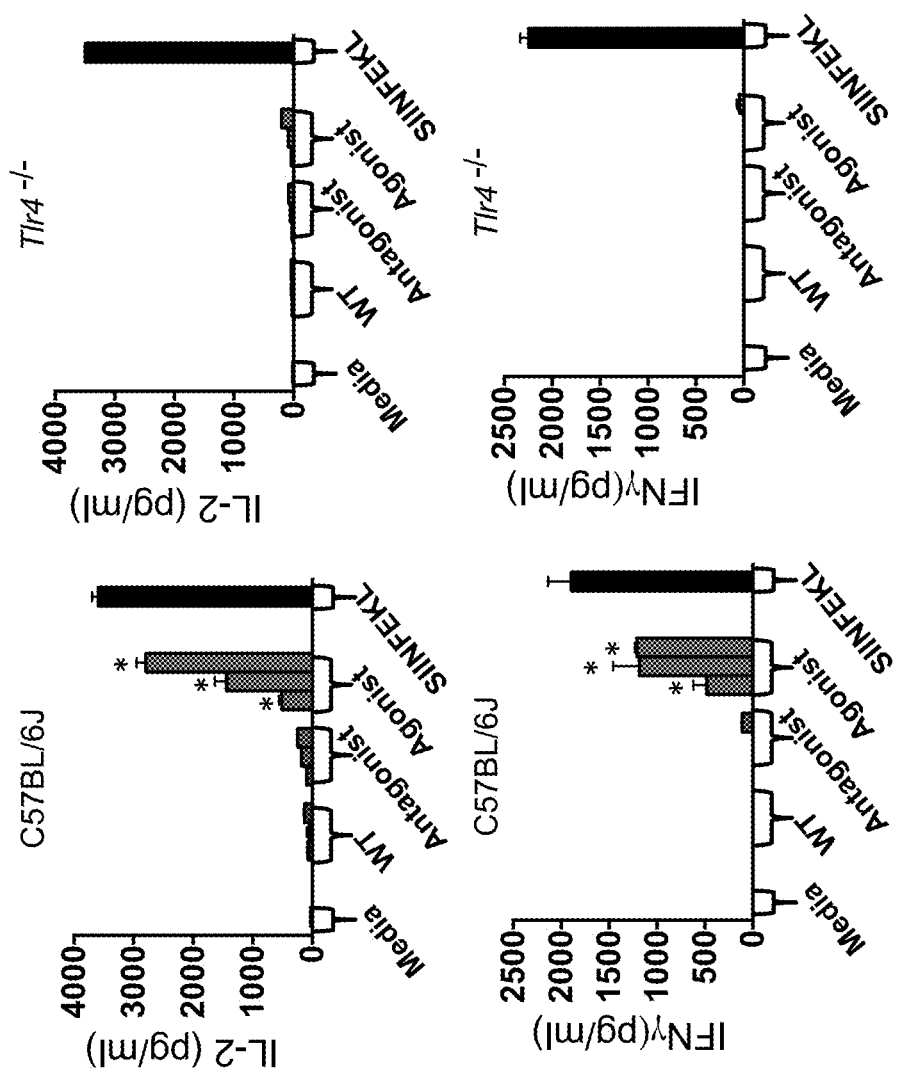
FIGS. 11A-11B demonstrate that *P. gingivalis* strains expressing defined lipid A structures can be used to modulate antigen-specific immune responses. C FIG. 19 demonstrates that treatment of DCs with *P. gingivalis* LPS species enhances cross-presentation of peptides derived from antigens internalized by endocytosis and phagocytosis. DCs were treated with media alone or LPS from *P. gingivalis*, *B. thetaiotaomicron* or *E. coli* (100 ng/ml) for 16-18 hr. DCs were pulsed with graded doses of soluble OVA (sOVA) or bead-bound OVA (bbOVA) for 1 hr and then co-cultured with CTV-labeled OT-I T cells. Cells pulsed with the pre-processed SIINFEKL (SEQ ID NO: 1) peptide (0.01 ng/ml) served as controls. The frequency of proliferating T cells was assessed by flow cytometry after 72 hr. Data represent the mean±SD of triplicate samples from one representative of three independent experiments.
Figure 11B:
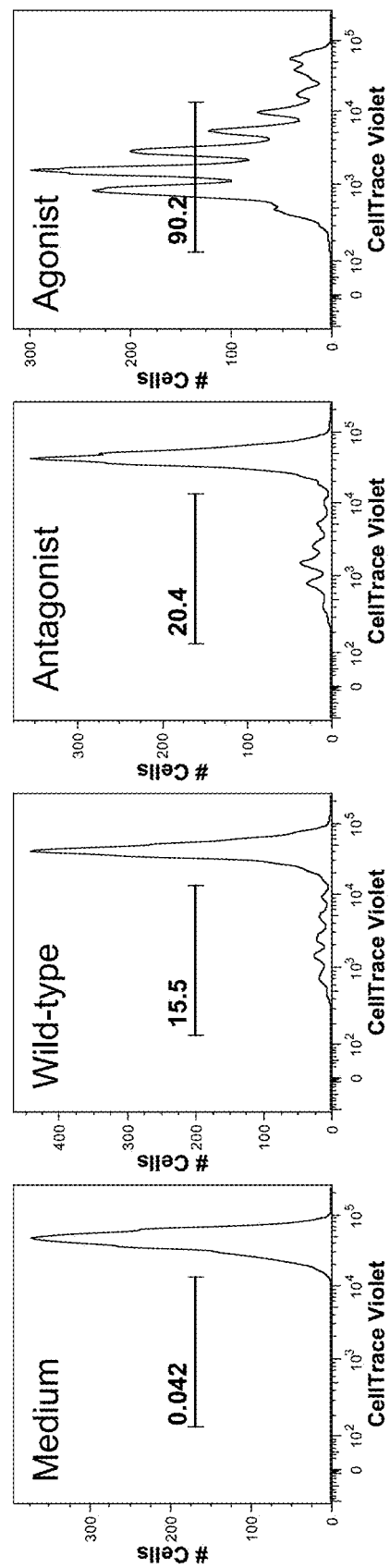
Figure 12:
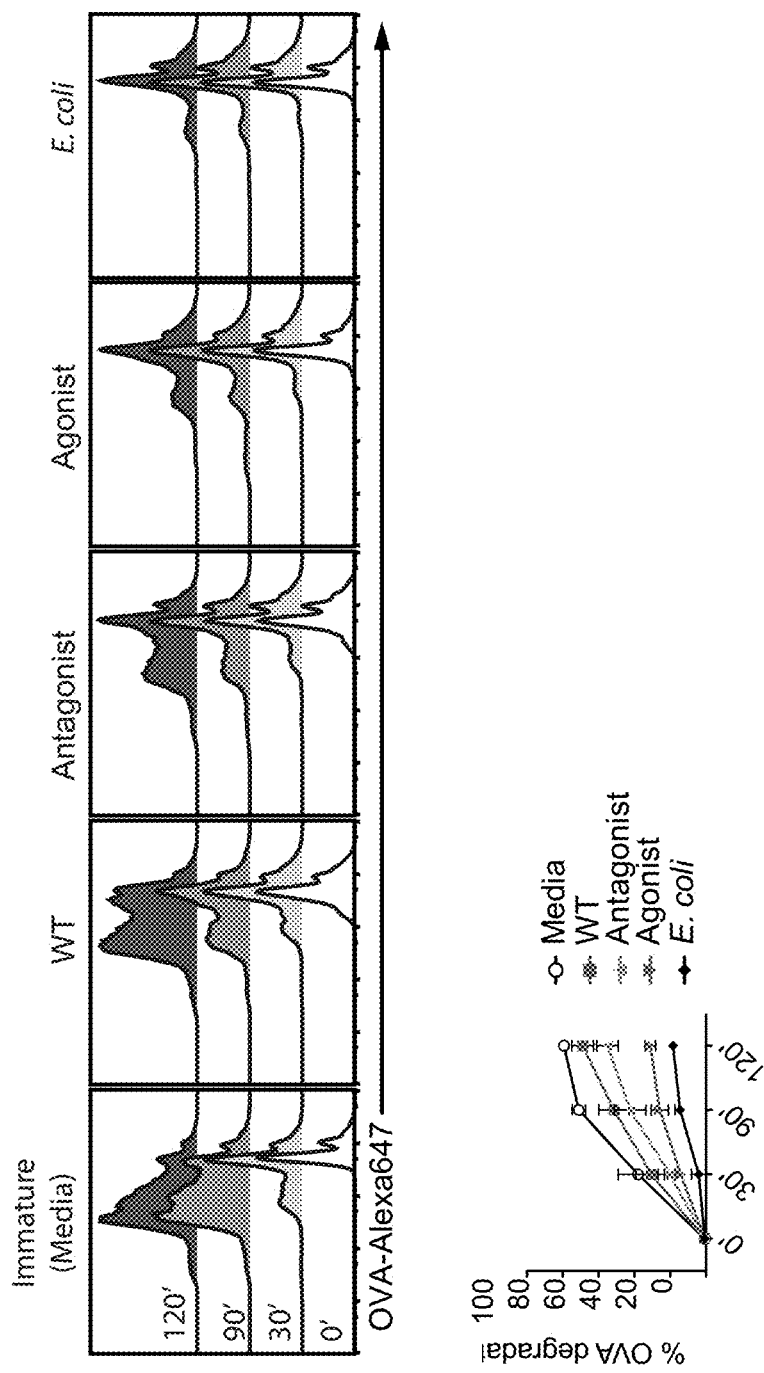
Figure 13:
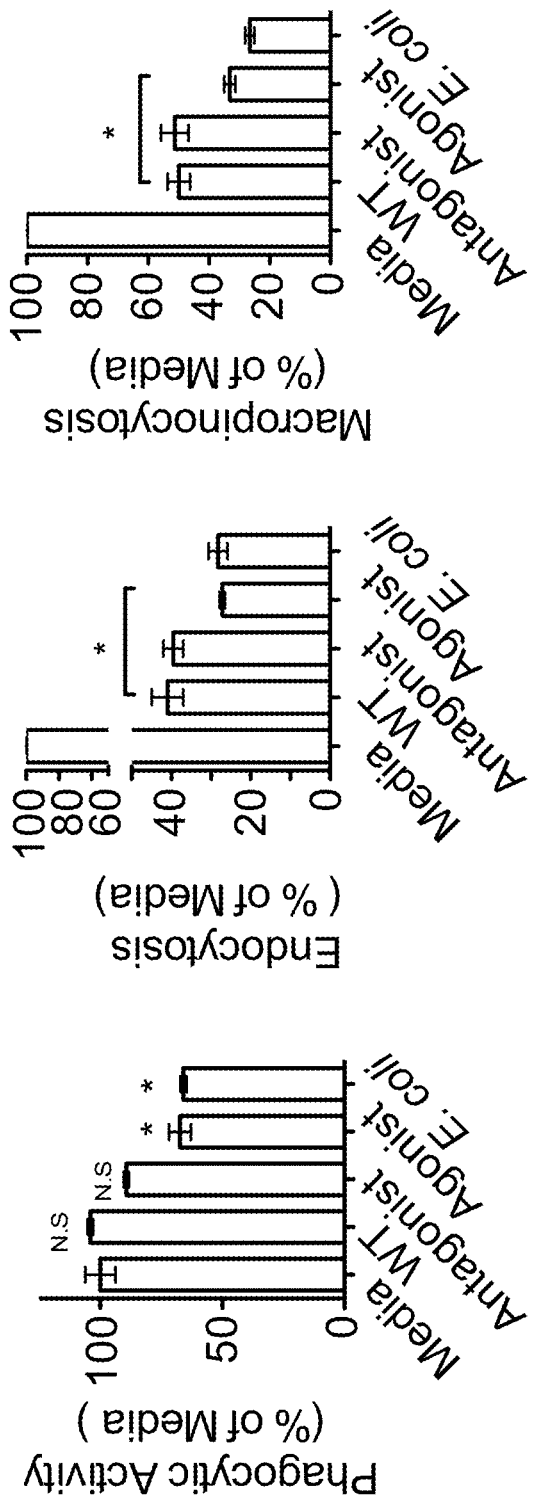

Consistent with these results, secretion of IL-2 and IFNγ by OT-I T cells was only observed when co-cultured with BMDCs treated with the agonist strain (FIG. 11), and was dependent on TLR4 (FIG. 11). However, expression of CD69, an early marker of T cell activation, was induced by BMDCs treated with the *P. gingivalis* agonist and antagonist strains (FIG. 10) and this was largely TLR4-dependent (FIG. 10). These results indicate that the agonist strain efficiently induces cross priming of naïve CD8 T cells. Importantly, DCs treated with the wild type and antagonist strains induce initial activation of T cells, reflected in the up regulation of CD69, but fail to induce full T cell activation that leads to proliferation and IFNγ secretion. This aborted activation may be due to the induction of tolerogenic DCs by these strains, which rather than priming T cells, induce immune tolerance [31].

Figure 5:
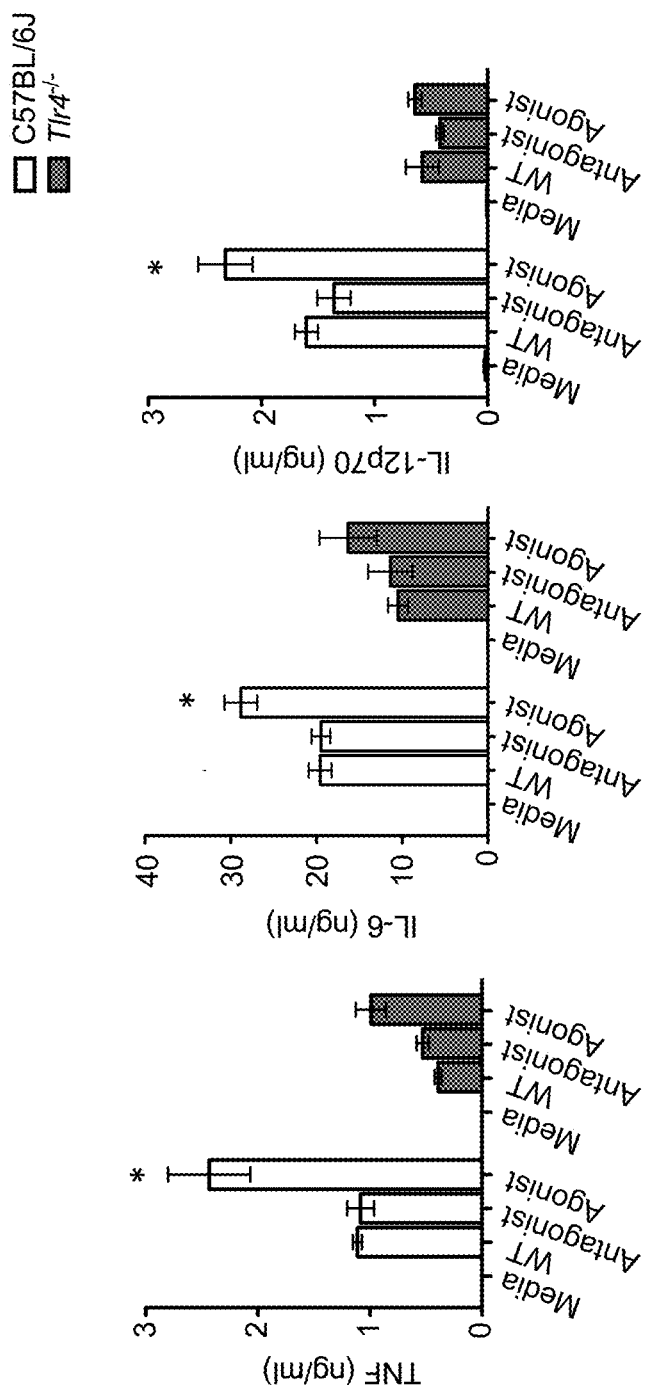
FIG. 5 shows that *P. gingivalis* strains expressing divergent lipid A structures elicit a similar pattern of pro-inflammatory cytokine production by dendritic cells. Bone marrow-derived dendritic cells (herein referred to as DCs) from C57BL6/J and Tlr4$^{-/-}$ mice were treated with *P. gingivalis* strains (MOI 10) for 18-20 hr. Levels of TNF, IL-6, and IL-12p70 in cell culture supernatants were measured by ELISA. *p<0.0001 Agonist vs. WT by two tail t-test. C57BL/6J vs. Tlr4$^{-/-}$ was significant (p<0.0002) for all strains and cytokines. Data represent the mean±SD of triplicate samples from one representative of three independent experiments.
Figure 7:
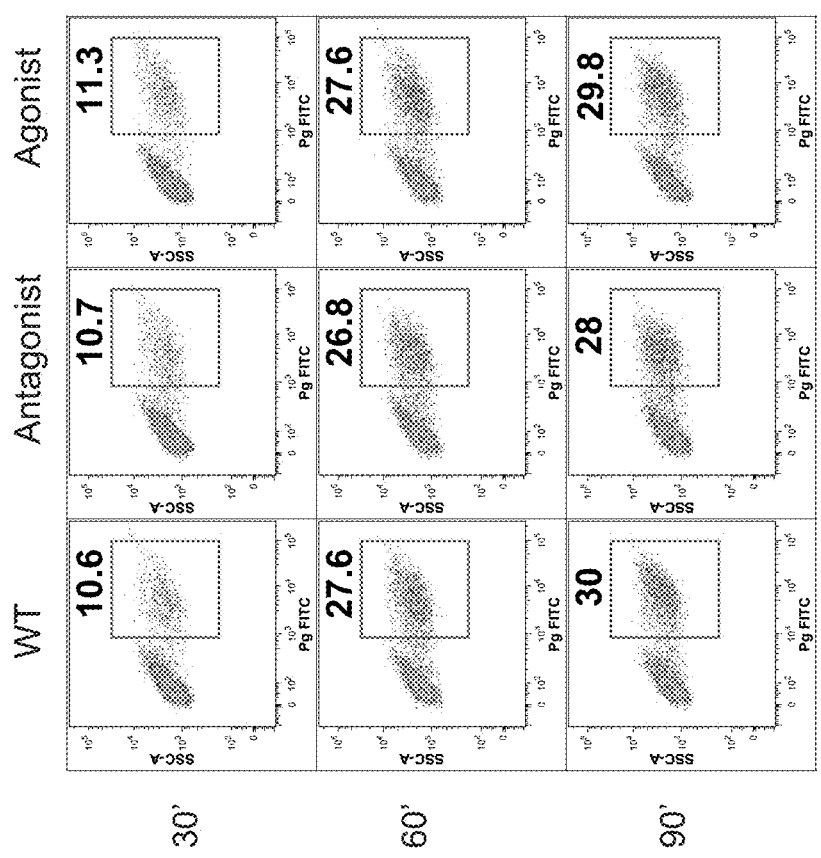
FIG. 7 demonstrates *P. gingivalis* strains are internalized similarly by DCs, and thus, differences in immune responses cannot be attributed to differences in bacterial uptake. WT BMDCs were stimulated with the indicated fluorescently labeled *P. gingivalis* strains (MOI 10) for 30', 60', or 90' and uptake assessed by flow cytometry. Data are representative of three independent experiments with similar results.
Figure 8:
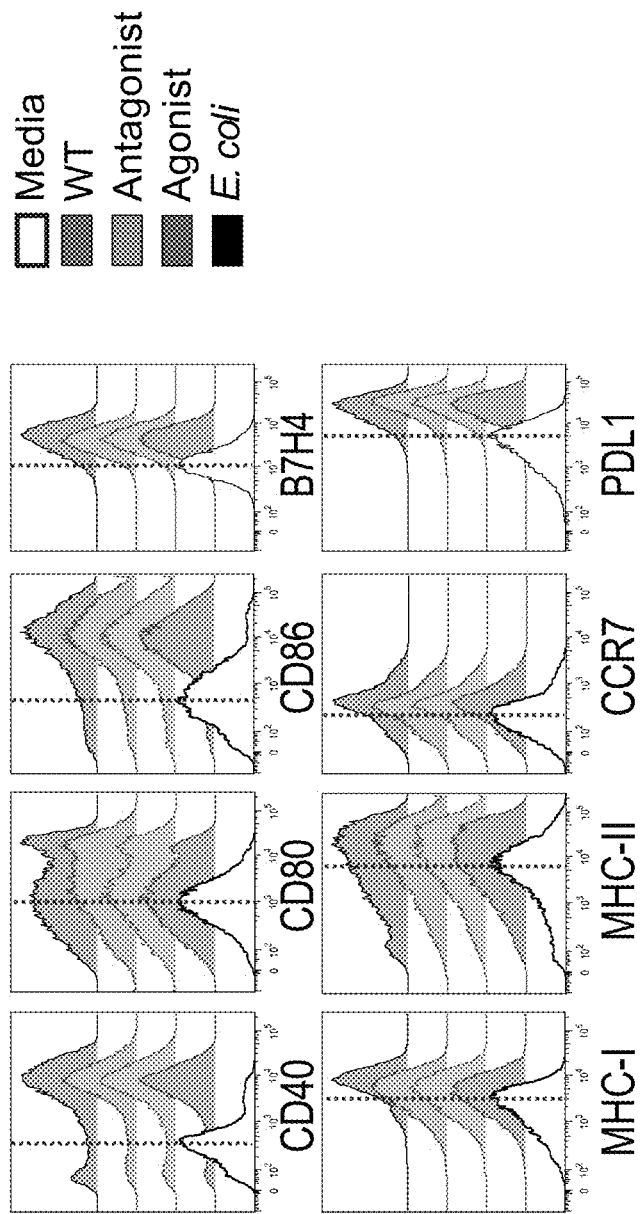
FIG. 8 demonstrates that *P. gingivalis* strains induce the phenotypic maturation of DC independent of the lipid A species expressed. DCs were stimulated with *P. gingivalis* strains (MOI 10), *E. coli* (MOI 10) or media alone for 18 hr. Surface expression of co-stimulatory molecules (CD40, CD80, CD86), co-inhibitory molecules (B7-H4, PD-L1), MHC complexes (MHC-I, MHC-II), and the lymph node homing receptor CCR7 were analyzed by flow cytometry. Histogram overlays are shown for each marker. A dashed line was drawn arbitrarily for reference. Results are representative of three independent experiments. All *P. gingivalis* strains induced comparable expression of maturation markers.
Figure 9A:
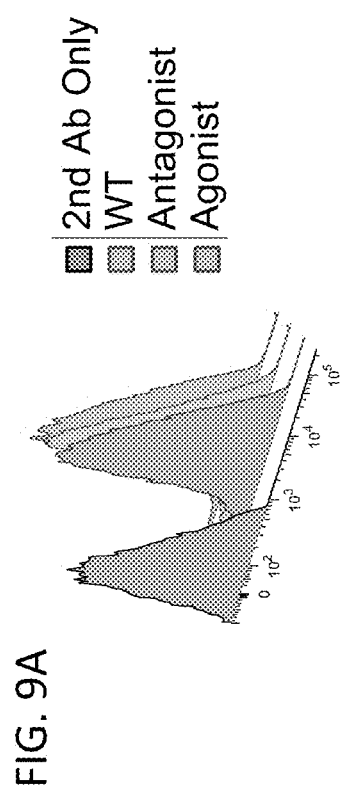
FIGS. 9A-9B depict flow cytometry analysis of OVA-coated *P. gingivalis* strains. Ovalbumin (OVA) was used as a model protein to assess the utility of *P. gingivalis* strains as microbial vectors for antigen delivery and immune modulation. Heat-killed *P. gingivalis* strains ($10^9$/ml) were coated with 2 mg/ml of OVA overnight at 4° C. on a rotating wheel. Bacteria were washed three times with PBS and stained with a 1/750 dilution of a polyclonal rabbit anti-OVA antibody followed by an Alexafluor647-conjugated anti-rabbit IgG. OVA coated bacteria incubated with secondary antibody alone were used as controls.
Figure 9B:
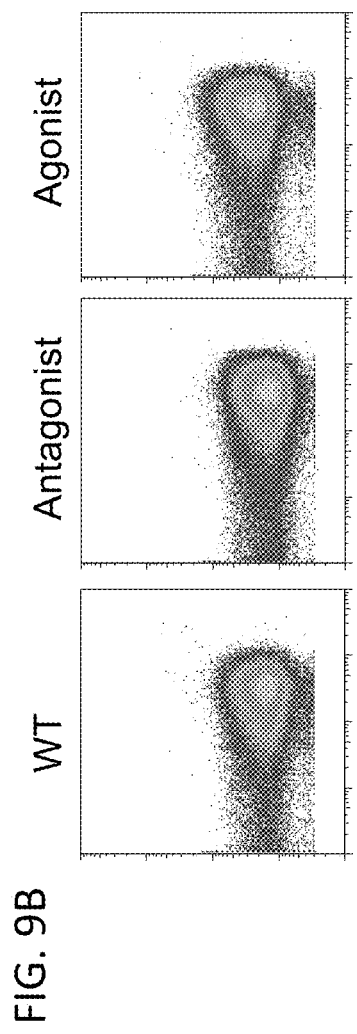
Figure 14:
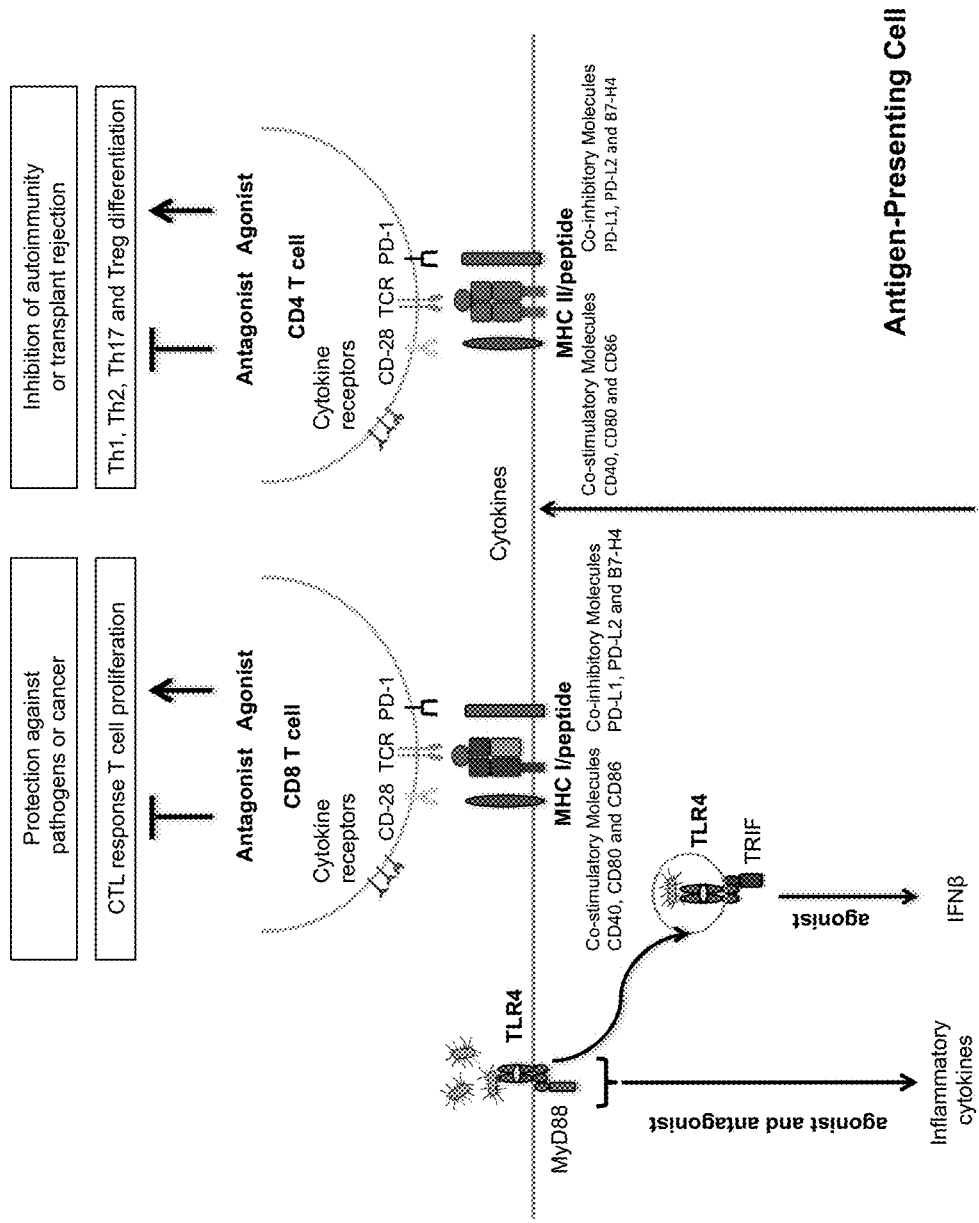
Figure 15:
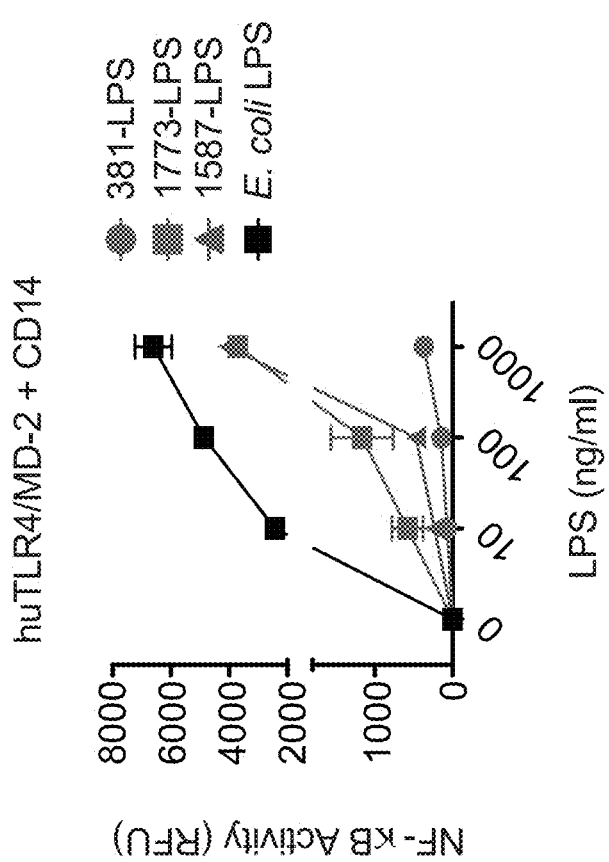
Figure 16:
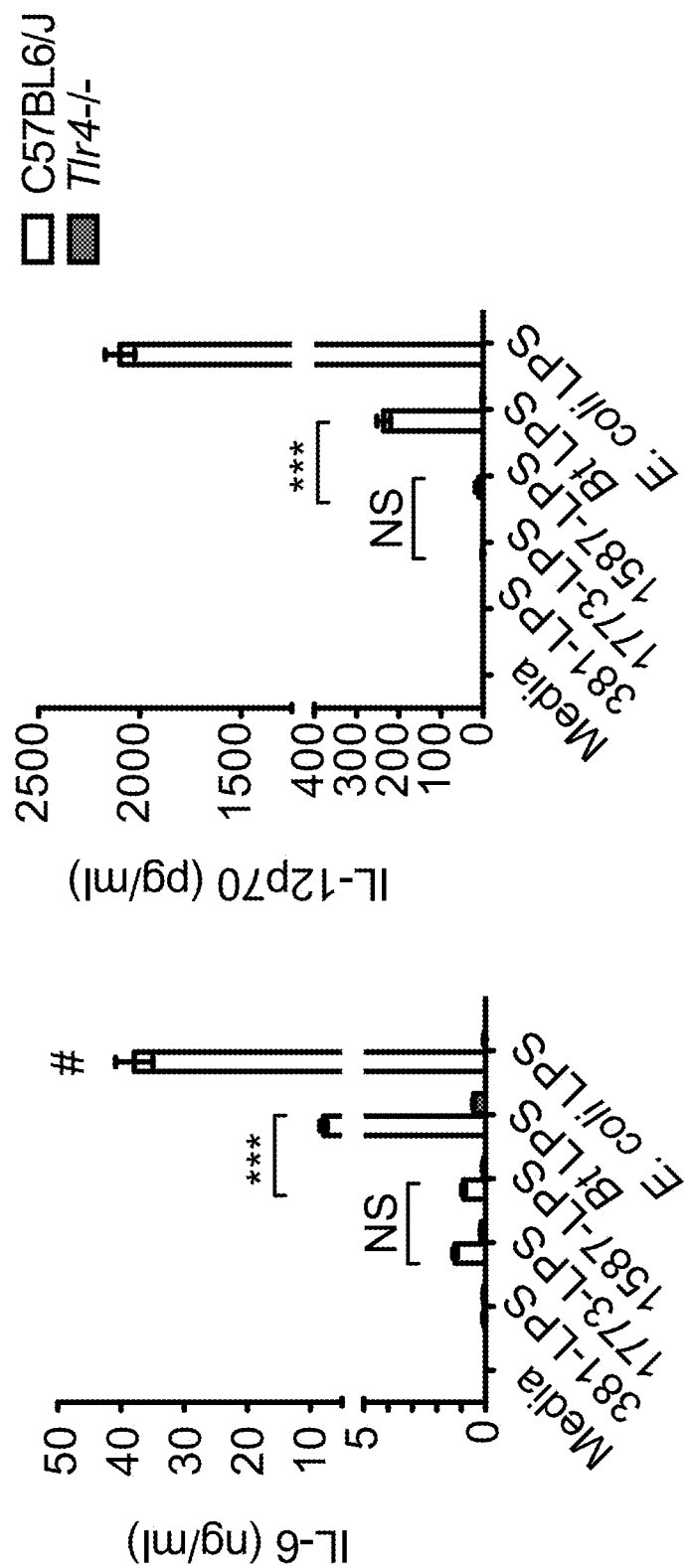
Figure 17:
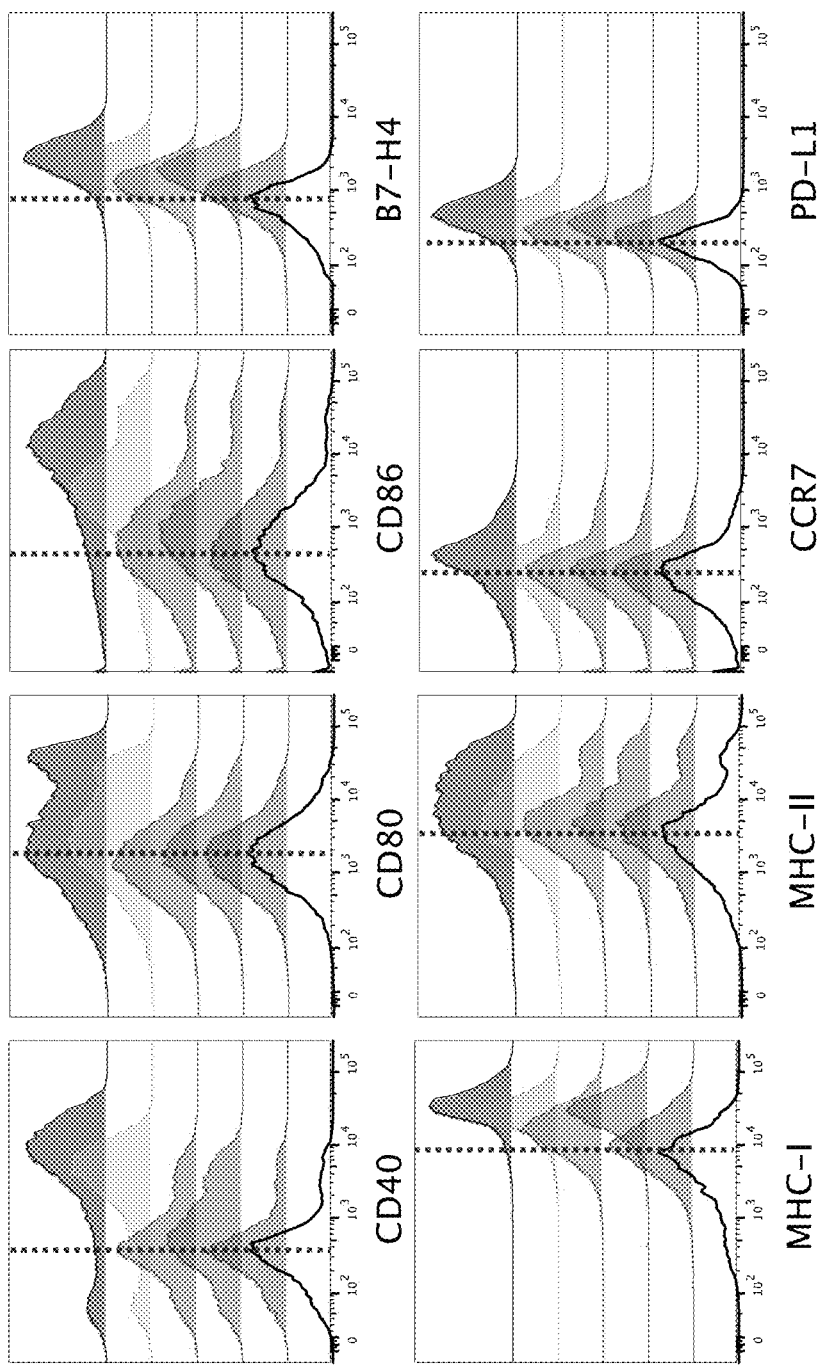
Figure 18:
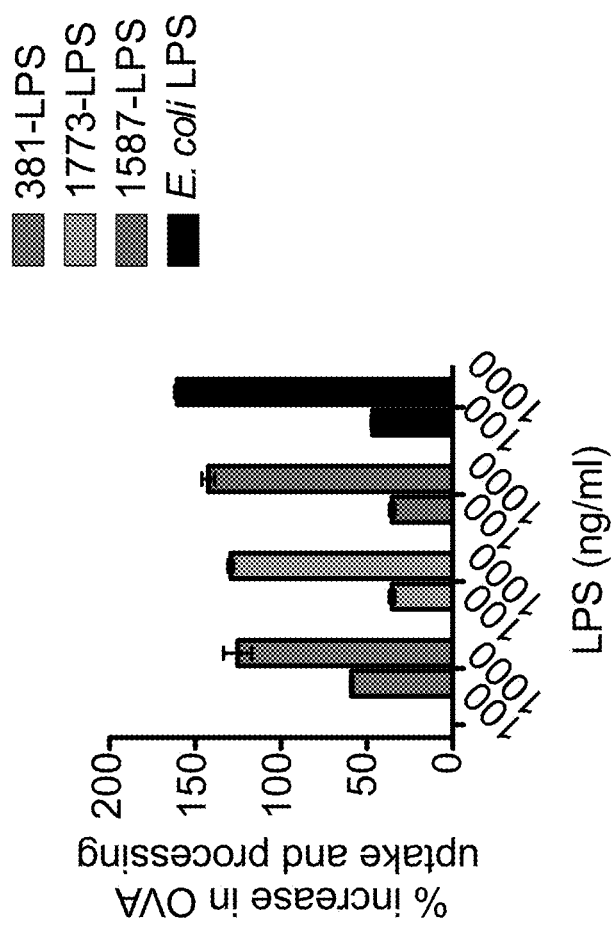
Figure 19:
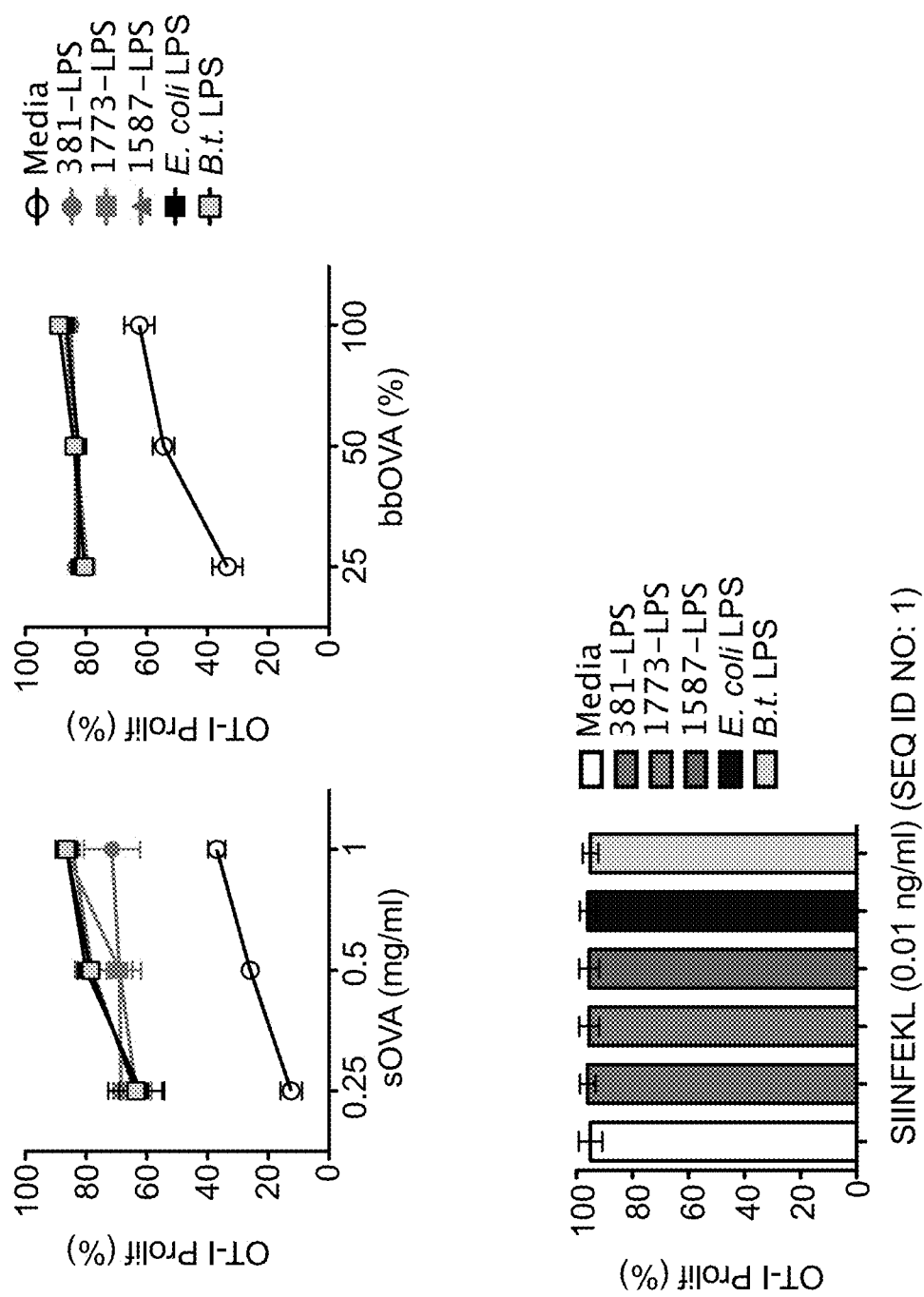
Figure 20A:
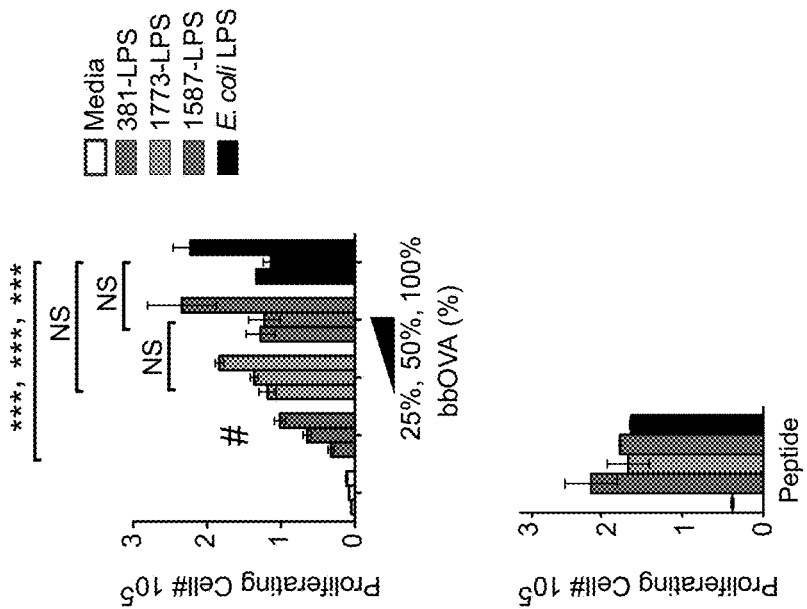
FIGS. 20A-20B demonstrate that the lipid A component of LPS modulates CD8 T cell responses to cross-presented peptides. DCs treated with LPS from *P. gingivalis* or *E. coli* (100 ng/ml; 16-18 hr) or media alone were pulsed with graded doses of bbOVA or the SIINFEKL (SEQ ID NO: 1) peptide (0.01 ng/ml) for 1 hr and then co-cultured with CTV-labeled OT-I T cells. IL-2 and IFNγ secretion by OT-I cells in 18 hr culture supernatants was measured by ELISA (FIG. 20A). The absolute number of live proliferating T cells was determined by flow cytometry after 72 hr (FIG. 20B). Data represent the mean±SD of triplicate samples from one representative of three independent experiments. *p<0.05, p<0.01, *p<0.0001; # **p<0.01 NP-LPS versus all other LPS variants by two-way ANOVA with Bonferroni's post-test.
Figure 20B:
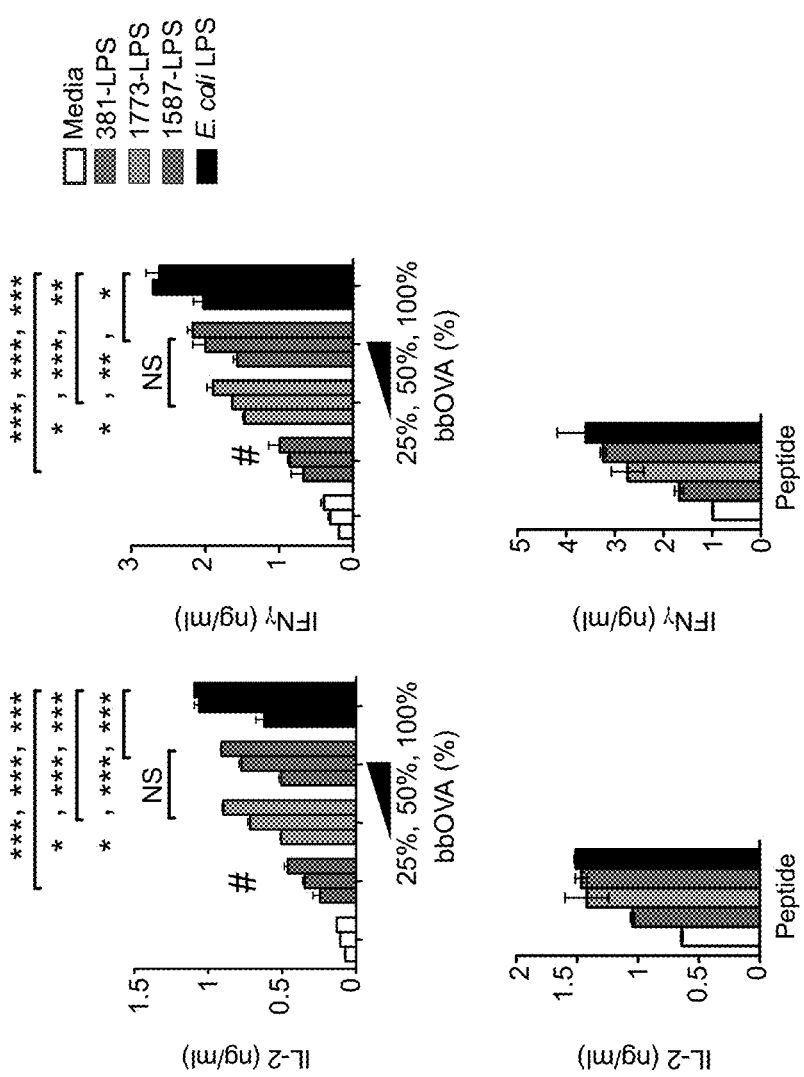
Figure 21A:
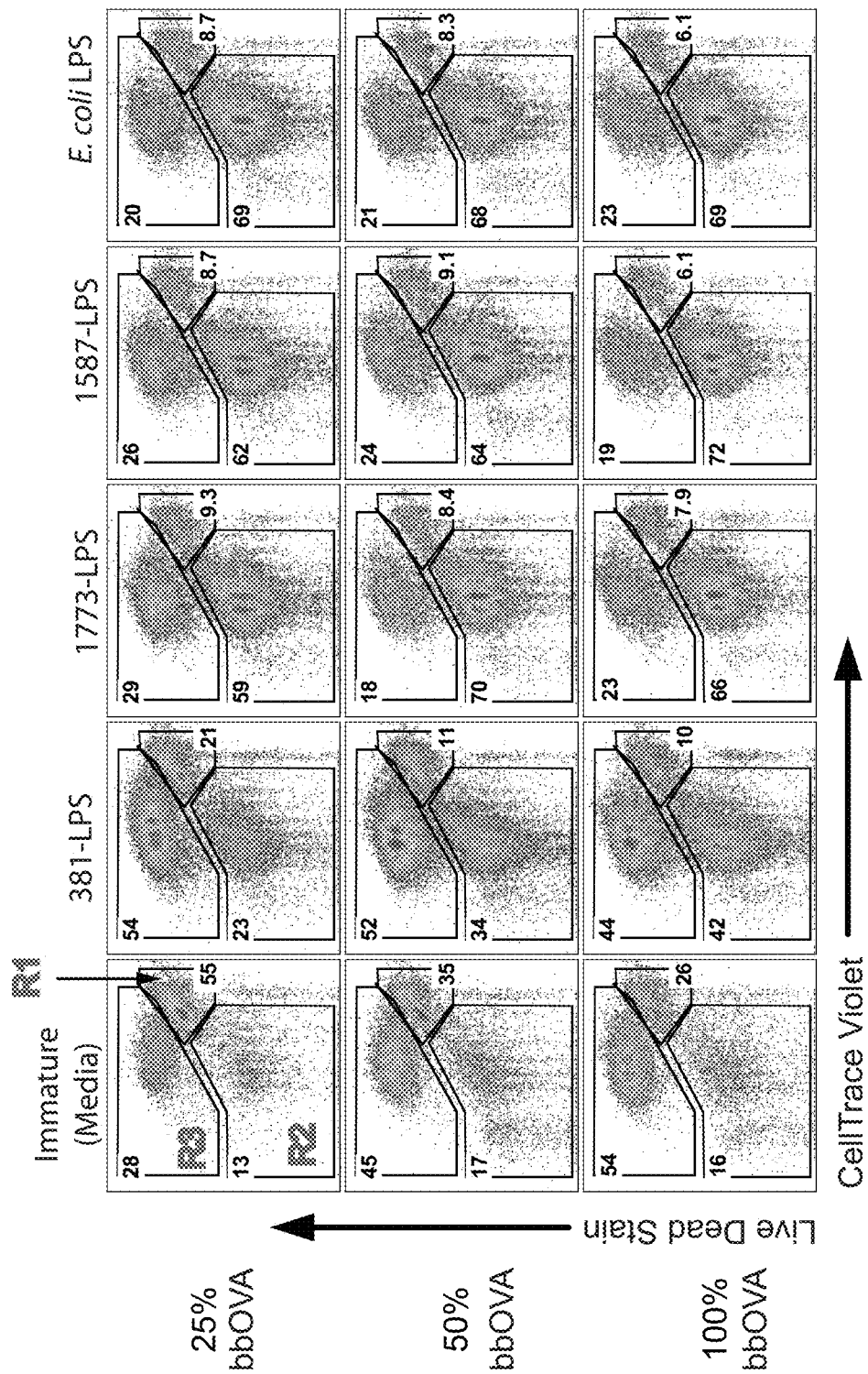
Figure 22:
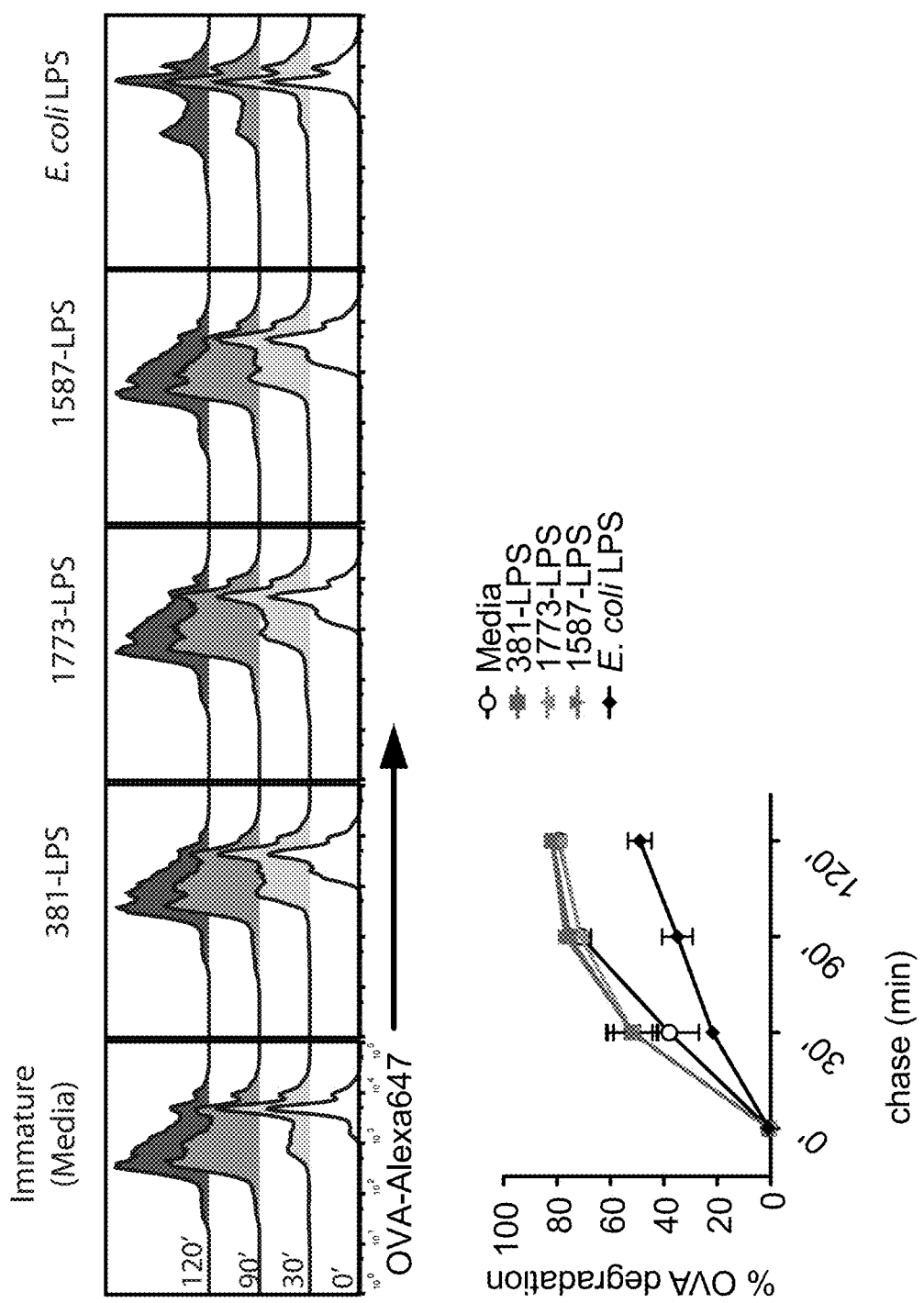
FIG. 22 demonstrates that LPS structure modulates the rate of phagosomal antigen degradation. DCs were treated with *P. gingivalis* or *E. coli* LPS (100 ng/ml) or media alone for 16-18 hr before phagocytosis of bbOVA. Phagosomal degradation of OVA was analyzed by flow cytometry after different chase periods. Representative histograms are shown for each time point and condition. A graphical representation of pooled results from two of three independent experiments is shown. Percent degradation was calculated by measuring the amount of remaining OVA on beads compared to beads at 0'. Results demonstrate that DCs treated with *P. gingivalis* LPS species degrade phagosomal antigens at an accelerated rate as compared to *E. coli* LPS.
Figure 23:
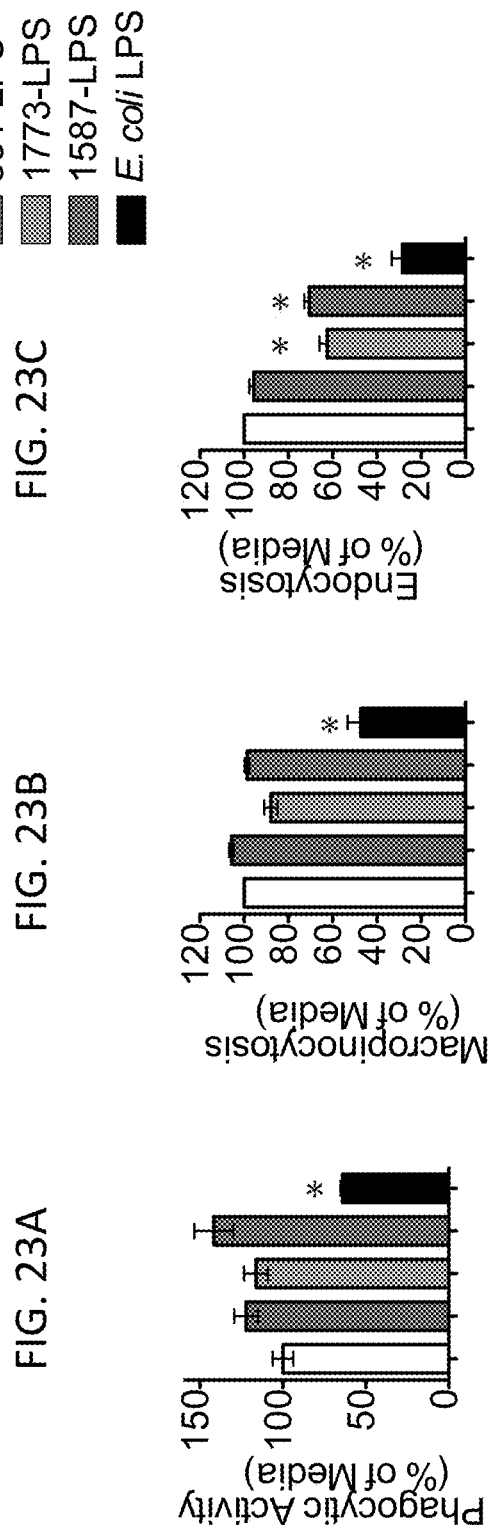
FIGS. 23A-23C demonstrate that LPS structure regulates the endocytic activity of DCs. DCs were treated with LPS isolated from the indicated strains (100 ng/ml) or media alone for 16-18 hr. Phagocytosis (FIG. 23A), macropinocytosis (FIG. 23B), and endocytosis (FIG. 23C) were assessed by flow cytometry. Results are expressed as percent activity relative to media treated immature DCs. Data represent the mean±SD of triplicate samples from one representative of three independent experiments. *p<0.05 by ANOVA. The data show that DCs treated with *P. gingivalis* LPS species retain their endocytic activity as compared to *E. coli* LPS.

These results imply that the agonist and antagonist strains modulate the immune responses by activating distinct arms of TLR4 signaling, with only the agonist strain able to induce robuts TLR4 signaling from intracellular compartments (FIG. 6). It is proposed that administration of the agonist strain, engineered to express a desired antigen such as a tumor antigen, will elicit a T cell response to this antigen that can be harnessed as an immunotherapy for a wide range of cancers (FIG. 14). It is proposed that the antagonist strain induces DCs to express immune-regulatory modulators such as co-inhibitory ligands (PD-L1, PD-L2 and B7-H4) or immune suppressive cytokines such as IL-10; thus this strain can be used in the treatment of a range of autoimmune diseases as well as to prevent transplant rejection (FIG. 5).

Multiple Advantages to the Proposed Microbial Vectors Including Broad Utility and Ease of Expression of Antigen of Interest:

The potential of *P. gingivalis* agonist ($1587_{381}$) and antagonist ($1773_{381}$) strains to modulate antigen-specific CD4 and/or CD8 T cell responses will be explored. The whole bacteria engineered to express the model antigen ovalbumin (OVA) will be used. The rationale for the use of intact bacteria rather than purified LPS is as follows: 1) Particulate antigens are more efficient than soluble antigens for induction of antigen cross-presentation, which is necessary for cross-priming or cross-tolerance of CD8 T cells [32].2) For TLR4-stimulated antigen presentation to CD4 T cells, antigens co-localized with LPS in a phagosome are more efficiently presented as compared to antigens in phagosomes devoid of LPS [33]. Using whole bacteria expressing an antigen of interest assures co-localization of the antigen with LPS. 3) The described engineered vectors will fill the need for personalized applications targeting patient-specific antigens, bypassing the requirement of expression and purification of targeted antigens. Significantly, this approach requires standard molecular cloning of cDNA into standardized expression plasmids for introduction into the appropriate bacterial strain.

The approaches described herein overcome existing challenges related to toxicity of administrating bacterial LPS and is based on whole bacteria with low endotoxicity. Specific agonist and antagonist strains to tailor T cell responses (potentiate or restrain) will be utilized. These microbial strains can be engineered to express a wide array of defined antigens to manipulate the immune system for specific therapeutic strategies. Such antigens include but are not limited to tumor antigens (Her2/neu), bacterial, viral, or self-antigens, and involve conditions such as cancer, infectious diseases, and autoimmunity. Antigens can be easily expressed recombinantly in *P. gingivalis*. The agonist strain can be used as a vaccine adjuvant to stimulate an immune response against a select antigen of interest such as an antigen associated with a tumor or infectious disease. Likewise, the antagonist strain can be engineered to express specific self-antigens associated with a broad array of autoimmune diseases. Significantly, these antigens could be tailored for patient-specific responses in both the agonist and antagonist strains. Thus there are numerous advantages to this approach with the potential for broad therapeutic impact in the treatment of infectious, neoplastic, and autoimmune diseases.

Compared to other types of vaccine carriers, bacteria based antigen delivery vectors exhibit multiple advantages: i) the possibility to control virulence and immunogenicity ii) its non-integrative properties iii) the ability to regulate the amount and in vivo localization of antigen expression iv) the potential for multiple vaccine delivery routes and v) potent stimulation of the innate and adaptive immune systems. Several bacterial species have been developed and implemented for cancer immunotherapy, and several of these have demonstrated promising pre-clinical outcomes. These include the Gram-negative pathogen *Salmonella typhimurium* and the Gram-positive pathogen *Listeria monocytogenes*. To avoid potential lethality, both of these pathogens must be attenuated prior to their implementation. The benefit of the approach described herein is the use of a host-adapted pathogen which induces a potent immune response but exhibits extremely low toxicity, thus bypassing the need to attenuate virulence.

Experimental Plan

The focus is on developing bacterial vectors expressing specific antigens for the treatment of cancer, and transplant rejection. The utility of lipid A mutant strains that express the model antigen OVA (Approach 1) will be developed and tested in established models as novel therapeutics for inflammation augmentation in melanoma and breast cancer, and suppression in transplant rejection (Approach 2). In additional future studies, these microbial vectors can be developed for treatment of other inflammatory diseases by engineering them to express specific disease-associated antigens. The use of the agonist and antagonist vectors will allow for the targeting of these strains in numerous diseases to either potentiate or restrain T cell responses. The novelty and innovation of the approach is in the use of genetically modified strains of a common host-adapted pathogen to broadly manipulate the immune system for therapeutic potential.

Approach 1—Characterization of the Spectrum of DC Priming, Cross-Priming, and Tolerogenic Functions Induced by P. gingivalis Agonist ($1587_{381}$) and Antagonist ($773_{381}$) Strains Expressing a Model Antigen.

Initially, the spectrum of CD4 and CD8 responses induced by the agonist and antagonist strains will be characterized. The goal of this first approach is to characterize the ability of agonistic and antagonist strains to induce model antigen OVA-specific T cell functional responses. P. gingivalis strains expressing the model antigen OVA for which there are multiple tools to detect antigen-specific responses will be constructed; the ability of the microbial strains to prime CD4 and cross-prime CD8 T cell responses will be defined: the ability of the microbial strains to induce T cell tolerance will be defined; and these in vitro studies will be confirmed in a mouse model. It has been established that the agonist strain ($1587_{381}$) has clear potential for use in priming CD8 T cell responses. This microbial strain is relatively non-toxic but at the same time can drive activation of antigen-specific CD8 T cell responses in vitro. The antagonist strain ($1773_{381}$) failed to induce cross priming of CD8 cells, but it was not immunologically inert based on its ability to induce pro-inflammatory cytokine production and costimulatory molecule up-regulation. Although BMDCs treated with the antagonist strain failed to drive CD8 T cell proliferation or CD8 IL-2 or IFNγ production, this strain did induce CD69 expression, indicating partial activation. Based on these observations, it is proposed that the antagonist strain promotes T cell tolerance.

Construction of OVA-Expressing P. gingivalis and Antigen Cross Presentation and T Cell Proliferation:

The in vitro T cell priming studies performed to date have used P. gingivalis coated with OVA. However, for in vivo priming and immune-modulatory therapies, heat-killed bacteria engineered to express OVA is use. For foundational studies, both in vitro and in vivo, T cell responses to OVA using OT-I and OT-II mice are examined. Additionally, OVA-specific T cells are targeted, but in non-TCR transgenic mice with a normal TCR repertoire. Therefore, OVA-expressing $1587_{381}$ and $1773_{381}$ strains, to be designated $1587_{381}$-ova and $1773_{3R1}$-ova, are constructed. The E. coli/ P. gingivalis shuttle vector pTIO-1, which has been used to introduce exogenous DNA fragments up to 10 kb into P. gingivalis, is modified. pTIO-1 is modified as follows: 1) The ermF cassette encoding erythromycin resistance is replaced with the TetQ cassette [34] to allow selection with tetracycline instead of erythromycin. This is necessary since $1587_{381}$ and $1773_{381}$ lipid A phosphatases were mutated by insertion of ermF. 2) A multiple cloning site is created containing an upstream FimA promoter and downstream FimA terminator, to drive expression of cloned cDNAs. Elements from the FimA gene were chosen because this gene is highly expressed by P. gingivalis [35]. OVA expression is confirmed by Western blot analysis. Issues related to the stability of OVA expression under various antibiotic selection is unexpected, since once expression is confirmed heat-killed bacteria is utilized. If difficulties are encountered expressing OVA using this plasmid, a targeting construct is designed to allow insertion of cloned cDNAs (regulated by FimA elements) into the P. gingivalis chromosome using homologous recombination. Using OVA-expressing agonist and antagonist strains, antigen cross presentation and T cell proliferation assays performed with OVA-coated bacteria as described (see FIG. 4) will be repeated. In vitro and in vivo studies using these newly constructed strains can be performed.

Priming of CD4 and CD8 T Cell Responses:

The ability of $1587_{381}$-ova and $1773_{381}$-ova to drive priming of CD4 cells in vitro is examined. Cross-priming of CD8 cells will be as described above except FACS-purified naïve MHC II-restricted CD4 OT-II cells will be used as responders. Proliferation will be measured (by dilution of CellTrace Violet) and intracellular cytokine staining will be performed to determine the nature of the CD4 response induced (Th1, Th2, Th17). It will be determined if there is induction of Tregs by staining for CD25 and intracellular staining of FoxP3. If significant induction of Tregs (FoxP3$^+$ CD25$^+$) is observed, additional studies to assess the in vitro suppressor activity of these Tregs is performed. Purified naïve OT-II cells are primed with BMDCs treated with P. gingivalis and CD4$^+$CD25$^+$ cells are purified from these cultures by magnetic separation and cultured at different ratios with CellTrace Violet-labeled CD4$^+$ T cells from C57BL/6J mice along with mouse T cell activator CD3/CD28 Dynabeads. Inhibition of cell proliferation will be determined based on inhibition of CellTrace Violet dilution. Since the purified CD4$^+$CD25$^+$ population contains all activated T cells, not just Tregs, these studies are only performed if the initial FoxP3 staining reveals a significant fraction of CD25$^+$ cells are also FoxP3 positive.

Induction of T Cell Tolerance:

In the cross-priming experiments described herein, it was observed that the antagonist strain resulted in the induction of aborted OT-I T cell activation. It is possible that this represents induction of an anergic response. If this is the case, it would imply that the antagonist strain expressing an appropriate auto-antigen could be used to induce anergy in auto-reactive T cells. This is significant and could be of broad therapeutic value in the treatment of several autoimmune diseases. To determine if abortively activated T cells are indeed anergic, the cells will be generated by co-culture with the antagonist strain as described above. T cells will then be purified by negative selection of BMDCs, rested, and restimulated by culture on plate-bound anti-CD3 and anti-CD28. Restimulation will be assessed by measurement of secreted IL-2. Analogous experiments will be performed with OT-I cells if there is evidence of T cell non-responsiveness in experiments with these cells.

Modifications for In Vitro Phase:

Approach 1 relies on standard in vitro studies. If in vitro experiments with heat-killed OVA-expressing strains fail to recapitulate the results obtained using heat-killed OVA-coated strains, differences in quantity or availability of ovalbumin expressed intracellularly vs. ovalbumin coated on the cell surface may be examined. Localization of ectopically expressed defined antigen epitopes, either on the bacterial surface, in the periplasmic space, or intracellularly, has been reported to have a minimal effect on the efficiency of MHC I or MHC II antigen presentation [39]. Therefore, the initial focus is on modulating expression levels. High levels of expression of a foreign protein could be toxic to the bacteria or otherwise alter bacterial characteristics. Conversely, low levels of expression could result in reduced efficiency of antigen presentation. RNA seq analysis of P. gingivalis grown in culture is available [35] allowing for the choice of a broad array of regulatory elements to modify expression levels. Another possible explanation for differences between OVA-coated and OVA-expressing bacteria could be that coated bacteria are heat-inactivated prior to incubation with ovalbumin, sparing ovalbumin the effects of heat denaturation. Exposure of OVA-expressing bacteria to heat will result in ovalbumin denaturation and, presumably, aggregation with other denatured intracellular proteins with unknown consequences for antigen processing. Therefore, other methods of bacterial inactivation, including formalin fixation and UV-irradiation, may be employed.

In Vivo Assessments:

To confirm results obtained in vitro, an in vivo system is used in which $5 \times 10^6$ purified naïve OT-I or OT-II T cells (Thy1.2) are transferred into C57BL/6J. Thy1.1 mice. This is necessary to avoid artifacts associated with the near monoclonality of the T cell repertoire of OT-I and OT-II mice. Thy1.1 recipients are used to allow identification and purification of transferred Thy1.2 cells. One day after transfer, mice will be immunized subcutaneously (SC) with heat-killed strains $1587_{381}$-ova or $1773_{381}$-ova. Subsequently, transferred OT-I or OT-II cells will be purified from lymph nodes and spleen by FACS sorting Thy1.2$^+$ and CD4$^+$ or CD8$^+$ cells. For OT-II cells, the cells are restimulated in vitro with plate-bound anti-CD3 and anti-CD28 and intracellular cytokine staining is performed to determine the nature of the response-Th1, Th2, or Th7. The frequency of OT-II Treg cells is determined by intracellular FoxP3 staining of cells. To determine if immunization induces differences in the functional suppressor activity, ex vivo suppressor activity of sorted splenic Thy1.2$^+$CD4$^+$CD25$^+$ cells is measured by culturing at different ratios with CellTrace Violet-labeled CD4$^+$ T cells along with mouse T cell activator CD3/CD28 Dynabeads. Suppressor activity will be determined by inhibition of CellTrace Violet dilution. Priming of CD8 T cell responses leads to a rapid expansion of antigen-specific CD8 cells. To measure OT-I cell responses to immunization with OVA-expressing strains, OT-I cells will be labeled with CellTrace Violet before adoptive transfer and cell proliferation post-immunization determined by FACs analysis of CellTrace Violet after harvest. Induction of OT-I CTL activity will be assessed by measuring killing of OVA-expressing E.G7-OVA lymphoma cells ex vivo using an LDH assay to measure LDH released into the medium by dead cells lymphoma cells.

Modifications for In Vivo Phase:

If in vivo administration of the *P. gingivalis* strains fails to recapitulate in vitro OVA-specific T cell functional responses, the dose of bacteria, route of administration (intravenous (IV) or intraperitoneal (IP), and frequency and timing of injections may be varied. If weak/moderate effects on OVA-specific T cell functional responses are observed, responses may be boosted with adjuvant treatment. In the case of failed in vivo activation of T cell responses observed, antibodies may be co-administered to block the checkpoint inhibitor PD-1. In the case of a failure to observe in vivo immune suppression that was obtained in vitro. PD-L1 Fc fusion protein may be co-administered to induce PD-1-mediated immune suppression. There is strong supporting data for the use of the agonist strain for cross-priming a CD8 response. Irrespective of the results obtained with the antagonist strain, it is anticipated that construction of the agonist strain expressing OVA can be tested immediately in mouse disease models of melanoma and breast cancer in Approach 2.

Approach 2: Investigate the Utility of Agonist and Antagonist Strains in Murine Models of Cancer and Transplant Rejection.

Immune Activation—Immunotherapy for Melanoma and Breast Cancer

Cancer remains a major source of morbidity and mortality with 17.5 million cases and 8.5 million deaths worldwide in 2015 [40]. For nearly 3 decades, cancer research has focused on identifying the genetic mutations that are responsible for driving malignant cell behavior. As such, anti-cancer treatments have emphasized targeting either the proliferation of cancer cells or the specific molecular basis driving their growth (e.g. cytotoxic chemotherapy, radiation therapy, and molecular targeted therapy). However, the recent success of immunotherapy in the treatment of melanoma and non-small-cell lung cancer, two tumor types that are traditionally recalcitrant to traditional forms of therapy, has provided direct clinical proof that cancer can be treated through the modulation of immunity [41, 42]. Immunotherapy development currently tends to focus broadly on three treatment categories: chimeric antigen receptor (CAR) T-cell therapies, vaccines, and checkpoint blockade strategies [43]. Tumor types such as melanoma, which exhibit a high immune infiltrate, are those that are most responsive to immunotherapy. Most solid tumors however, exemplified by breast cancer, exhibit a relative paucity of nearby T cells, which limits the potential of immunotherapy [2, 5, 44]. Overcoming this issue represents one of the most important rate-limiting steps for the broad application and effectiveness of immunotherapy.

Mouse models of cancer are valuable predictors of immunotherapy [45-49]. Significantly, mouse studies of immune evasion and immune editing have been predictors of responses to immunotherapy in humans [48, 49]. The most commonly used model consists of the inoculation of histocompatible cancer cell lines into immunocompetent inbred mice, generally from C57Bl/6 or BALB/c strains [45, 50]. Transgenic mice also yield highly useful models of genetically controlled cancers that provide important insights into the relationship between cancer and the immune system. Several groups have created mouse and humanized models of breast cancer that genetically, molecularly, biologically, and histologically recapitulates the formation and progression of the disease and mirror immune responses of tumors in patients [51-67]. Likewise unique genetic mouse models of melanoma that exploit common genetic drivers of human melanoma (e.g. BRAFV600E) to produce a faithful and reproducible model of cutaneous melanoma have been developed. These melanomas occur spontaneously dependent on a BRAFV600E transgene, and the rate and penetrance of melanoma is increased by additional mutations or by UV irradiation, consistent with human melanoma [68-71]. Moreover, these tumors are inherently metastatic to the lung and liver, and cell lines derived from these melanomas reproducibly form primary tumors and metastatic lesions in the lung, liver, and brain when reintroduced into syngeneic hosts ([72]; McRee and Hinds, unpublished). The SM1 cell line derived from the BRAFV600E mouse is an important complement to the B16 murine melanoma cell line commonly used in preclinical studies of melanoma, and both have proved invaluable in assessing in vivo responses to immunotherapies [73, 74]. Accordingly, the syngeneic C57Bl/6 or BALB/c breast cancer and melanoma lines developed, studied, and optimized are utilized to study immune activation. These models are used to establish whether melanomas and breast tumors growing in vivo can be targeted using recombinant strains expressing defined lipid A moieties and OVA as a novel form of immunotherapy.

Murine Model for Melanoma:

The B16-OVA murine melanoma cell line is used as a model. To allow for live imaging, B16-OVA cells are used that have been engineered to express luciferase. The ability of engineered agonist strain expressing OVA to elicit an anti-tumor immune response will be tested. To determine whether an agonist strain can prevent melanoma tumor growth, mice will be immunized as described herein and then injected SC with B16-OVA melanoma cells. Once a tumor is established in non-immunized, control animals (15 days post injection) tumor size will be determined. Tumor volumes will be measured daily until humane endpoint is reached, at which time tumors will be collected for pathologic study and for determination of infiltration of specific immune cells as evaluated by flow cytometry. The impact of vaccination with the agonist strain on established tumors will also be determined in which tumor growth is allowed to extend to ~2-5 mm as determined by calipers or imaging. Mice will then be immunized as described above and tumor size and degree of infiltration by immune cells will be determined as above. It will also be determined if these CD8 cells are functional ex vivo by CTL assays with B16-OVA cells as targets. Alternative approaches include altering the number of infections and injection routes for DC activation (orally, IP, IV, foot pad, number of injections) [75].

Murine Model for Melanoma Metastasis:

A. Tail vein injection of B16 melanoma cells, as well as genetically unique cell lines produced in the Hinds laboratory, are known to result in lung metastasis. The impact of vaccination with the agonist strain on tumor metastasis will be determined. Prophylaxis will be performed as above, which is analogous to preventing further seeding once a primary cancer is detected, and also allow colonization of the lung first followed by treatment. Imaging will be used to detect metastases when they are fairly substantial. At defined end points, lungs will be removed and imaged to quantify micro metastasis/residual disease in mice showing lack of continued metastatic growth. Previous studies support the general concept that immunization with B16 tumor antigens can reduce metastatic disease, largely through $CD8^+$ T cell activity [76]. B. Intracardiac injection of melanoma cells results in metastasis to brain, lung, bone, and liver. Ultrasound-guided intracardiac injection of melanoma cells will be performed using the Tufts University in vivo mouse imaging core. Treatment will occur prophylactically and/or after imaging reveals overt metastasis.

Murine OVA-B6 Mammary Tumor Model:

Three complementary mouse mammary tumor models are used. (1) The E0771 murine breast cancer cell line that was isolated from a medullary breast adenocarcinoma isolated as a spontaneous tumor from a C57B1/6 mouse [77, 78] and engineered to express GFP. (2) To complement this line, additional B6 mammary tumor lines that express SV40 with Kras and GFP in normal mouse mammary epithelial cells and form spontaneous tumors in vivo will be utilized. (3) The COMMA-D murine breast cancer cell line that was created from immortalized mammary epithelial cells isolated from a BALB/c and engineered to express firefly luciferase and transformed by serial passaging. All lines have been characterized and serially transplanted. OVA will be overexpressed in these tumor cell lines (E0771-OVA, SV40/KRas-OVA, COMMA-D-OVA) and their tumorigeneicity and regression orthotopically will be assessed in vivo. Accordingly, mice will be immunized as described herein and then injected orthotopically with E0771-OVA, SV40/KRas-OVA, or COMMA-D-OVA breast cancer cells. Tumors will be established 20 days post injection and tumor size determined by GFP expression and infiltration of specific immune cells evaluated by flow cytometry. The impact of vaccination will be determined on established tumors that have grown ~2-5 mm in diameter determined by calipers or GFP imaging. The mice will then be immunized as above and tumor size and degree of infiltration by immune cells will be determined as above. As described above, it will be determined if these CD8 cells are functional ex vivo by CTL assays. Injection route may be altered if necessary.

Modifications to Immune Activation Phase:

The B16 murine melanoma model is well established and has been used successfully to monitor responses to immunotherapy in both cutaneous (primary) and metastatic sites. However, efficacy of response, particularly in metastatic sites, may be limited by the ability of a subset of stem cells to eliminate or reduce the expression of the model tumor antigen, OVA. Further, B16 cells may not represent the full complement of genetic susceptibilities present in murine models that more faithfully recapitulate human disease. To address these issues, the microbial vectors can be readily adapted to target an endogenous melanoma tumor antigen, such as Cripto-1, that is present on a crucial metastasis seeding fraction of B16 cells and that is expected to be present in varying fractions of the cell lines derived from BRAFV600E-driven tumors [76]. In the event of partial responses or those that indicate recurrence due to loss of tumor antigen, the microbial vectors can also be readily adapted to produce multiple tumor antigens, decreasing the likelihood that an individual tumor cell would become invisible to all effector cells. The approach of using immunization against multiple tumor antigens has recently shown promise in human melanoma patients [79], although it is worth noting that the $CD8^+$ T cell responses were limited in this study, as was the durability of response of metastatic lesions vs. primary lesions. Therefore, the use of microbial vectors to produce a broad repertoire of $CD8^+$ T cells targeting multiple tumor antigens in the murine melanoma models described herein could significantly impact the formation and growth of metastatic disease.

As described above, mounting an immune activation that would lead to tumor regression might require multiple tumor antigens. If OVA is not sufficient, the human Her2 oncogene (as a naturally-occurring human cancer antigen) can be overexpressed in E0771-OVA cells. In addition, *P. gingivalis* can be engineered to express either SV40 or KRas and test those lines for T cell activation/cytotoxicity such that several tumor antigens will be targeted to impact tumor growth.

Immune Suppression—Transplant Rejection

Diseases caused by dysregulated immune activation, including autoimmune syndromes and allergy, remain a major health challenge. Autoimmune disease is estimated to afflict between 5% and 7% of the population in the developed world [80], while in the United States alone an estimated 60 million people suffer from allergies at a cost of about $20 billion per year [7]. Although there have been recent advances in treatment, notably the development of anti-TNF biologics, therapies to date induce non-specific immunosuppression resulting in potentially severe side effects [4]. A major advance in treatment of autoimmune syndromes would be the development of antigen-specific immune therapies—i.e. strategies to induce immune tolerance [6]. To date, perhaps the most well-studied examples of tolerance have been in transplantation [81]. Although the phenomenon of tolerance was first described in 1953 by Medawar and colleagues [82], induction of tolerance in the clinic has been challenging. Recent approaches such as costimulatory molecule blockade have failed to result in lasting graft survival [83] and are now used as alternative forms of immunosuppression but are limited by cost and complications associated with suppression of immunity. Tolerance remains a major goal in transplantation, autoimmunity, and inflammation because it has the potential to prevent unwanted immune responses without side effects while maintaining immunological memory to pathogen responses. Tolerance induction is used in a transplant model as a stringent test for the ability of the antagonist strain to induce antigen-specific immune suppression. This may validate use of the described vectors to induce tolerance in other clinically relevant situations such as autoimmunity, allergy, and asthma.

Transplant Model:

To test the ability of the antagonist strain to induce antigen-specific immune suppression, the well established Act-mOVA transgenic model is used [84]. In this C57/BL6-based model, OVA is expressed on the surface of most cell types. Engraftment of tissue from these mice onto non-transgenic C57BL/6 mice elicits a T cell-dependent anti-OVA response that leads to graft rejection [84]. The ability of the OVA-expressing antagonist strain to promote survival of Act-mOVA skin grafts on non-OVA expressing C57BL/6 mice will be determined. Recipient mice will be injected SC with the OVA-expressing antagonist strain and then transplanted with skin from OVA transgenic mice and normal littermate skin. Graft survival will be monitored daily by visual inspection. As a more clinically relevant test of successful prevention of graft rejection, the ability to induce tolerance to OVA transgenic skin in mice that have been sensitized to OVA will be examined. Mice will be transplanted with Act-mOVA skin and allowed to reject it. Several weeks later, mice will be given the OVA-expressing antagonist strain and challenged with a second Act-mOVA skin graft; graft survival will be monitored as above. These types of experiments will allow for the examination of the ability of this approach to prevent, as well as treat, pre-existing immune responses.

Modifications to Immune Suppression Phase:

If the antagonist strain promotes graft survival, studies to gain insights into the immune mechanisms will be performed. T-cell receptor transgenic mice specific for OVA albumin presented by MHC class I (OT-I mice) and MHC class II (OT-II mice) will be used to assess whether this approach leads to thymic deletion of OVA-specific T cells or the induction of peripheral tolerance and regulatory T cells. Together, the use of such models provides a stringent test of tolerance (i.e., the ability to induce life long-survival of OVA-expressing skin) or immunosuppression (the ability to prolong survival of OVA-expressing skin). This system explores what may be needed to improve the ability of the microbial vectors described herein to induce tolerance or improve immunosuppression. For example, whether administering the antagonist strain together with costimulatory molecule blockade leads to tolerance will be assessed. The use of lymphocyte subset depletion strategies may also be used to determine what may lead to resistance to tolerance or immunosuppression.

If the antagonist strain is demonstrated to prolong graft survival, this approach will be applied to models of allergy and autoimmunity. For allergy, the widely used mouse OVA-induced asthma model is used [85, 86]. This model features similarities to human disease, most notably the presence of eosinophilic lung inflammation, airway hyper responsiveness, and inflammatory cytokine production of IL-4, IL-5, IL-9, and IL-13 in bronchioalveolar lavage fluid mediated largely by CD4-Th2-mediated responses. Mice will be sensitized by IP injection of OVA followed by intratracheal delivery of OVA to induce asthma. The effect of injection of the OVA-expressing antagonist strain, either before the initial sensitization or between the sensitization and subsequent intratracheal OVA administration, will be assessed.

As a model of autoimmune disease, the myelin oligodendrocyte (MOG)-induced experimental autoimmune encephalomyelitis (EAE) model of multiple sclerosis is used 187, 881. In this model, an MOG peptide consisting of amino acids 35-55 is administered along with complete Freund's adjuvant and Pertussis Toxin to C57BL/6J mice to induce chronic non-remitting EAE. The ability of the antagonist strain, expressing MOG protein, to inhibit induction of EAE is tested, when administered either before or after MOG sensitization. Disease progress and severity will be assessed daily using a clinical score of 0-5 as follows: 0=no abnormality, 1=limp tail, 2=limp tail and hind limb weakness (legs slip through cage top), 3=hind limb paralysis, 4=hind limb paralysis and forelimb weakness, and 5=moribund.

SUMMARY

The use of genetically modified strains of a common host-adapted pathogen to manipulate the immune system for therapeutic potential is innovative and original. The approaches described herein utilize agonist and antagonist strains to tailor T cell responses (potentiate or restrain). These microbial strains can be engineered to express specific antigens to manipulate the immune system for therapeutic potential. These strains are engineered to express a model antigen as a proof-of-concept for a novel therapeutic paradigm for the treatment of model diseases that target both immune activation and suppression.

The approaches described herein may establish improved clinical approaches. New therapies that target specific immune activation/suppression pathways are vitally needed for the treatment of a broad array of immune-mediated disorders. These approaches are based on whole bacteria with low endotoxicity and overcome existing challenges related to the toxicity of administrating LPS and hence will induce fewer side effects experienced with LPS expressed by prototypic Gram-negative bacteria. It is anticipated that these microbial strains can be successfully engineered to express a wide array of antigens of interest and could be tailored for patient specific responses and will maximize therapeutic efficacy. These approaches have the potential to overcome issues with general systemic immune activation and suppression and to limit off target side effects of these interventions.

These approaches have the potential to produce a major impact in biomedical research. Recombinant microbial vectors expressing defined lipid A moieties and an antigen of interest can be harnessed for use as therapeutic vaccines to potentiate or restrain T cell responses for the treatment of a broad array of diseases (cancer, autoimmune, and infectious diseases). It is expected that these approaches will result in the generation of sufficient pre-clinical support for the development of a unique microbial vector system to modulate antigen specific immune responses for targeted immune therapy.

REFERENCES

1. Slocum, C., et al., Distinct lipid a moieties contribute to pathogen-induced site-specific vascular inflammation. PLoS Pathog, 2014. 10(7): p. e1004215.
2. Gras Navarro, A., A. T. Bjorklund, and M. Chekenya, Therapeutic potential and challenges of natural killer cells in treatment of solid tumors. Front Immunol, 2015. 6: p. 202.
3. Hartmann, J., et al., Clinical development of CAR T cells-challenges and opportunities in translating innovative treatment concepts. EMBO Mol Med, 2017.
4. Li. P., Y. Zheng, and X. Chen, Drugs for Autoimmune Inflammatory Diseases: From Small Molecule Compounds to Anti-TNF Biologics. Front Pharmacol, 2017. 8: p. 460.
5. Newick, K., et al., CAR T Cell Therapy for Solid Tumors. Annu Rev Med, 2017. 68: p. 139-152.
6. Pozsgay, J., Z. Szekanecz, and G. Sarmay, Antigen-specific immunotherapies in rheumatic diseases. Nat Rev Rheumatol, 2017.
7. Shurin, M. R, and Y. S. Smolkin, Immune-mediated diseases: where do we stand? Adv Exp Med Biol, 2007. 601: p. 3-12.
8. Couzin-Frankel, J., Breakthrough of the year 2013. Cancer immunotherapy. Science, 2013. 342(6165): p. 1432-3.
9. Shekarian, T., et al., Pattern recognition receptors: immune targets to enhance cancer immunotherapy. Ann Oncol, 2017. 28(8): p. 1756-1766.
10. Casella, C. R, and T. C. Mitchell, Putting endotoxin to work for us: monophosphoryl lipid A as a safe and effective vaccine adjuvant. Cell Mol Life Sci, 2008. 65(20): p. 3231-40.
11. Mata-Haro, V., et al., The vaccine adjuvant monophosphoryl lipid A as a TRIF-biased agonist of TLR4. Science, 2007. 316(5831): p. 1628-32.
12. McKee, A. S, and P. Marrack, Old and new adjuvants. Curr Opin Immunol, 2017. 47: p. 44-51.
13. Needham, B. D., et al., Modulating the innate immune response by combinatorial engineering of endotoxin. Proc Natl Acad Sci USA, 2013. 110(4): p. 1464-9.
14. Steimle, A., I. B. Autenrieth, and J. S. Frick, Structure and function: Lipid A modifications in commensals and pathogens. Int J Med Microbiol, 2016. 306(5): p. 290-301.
15. Tan, Y., et al., Mechanisms of Toll-like Receptor 4 Endocytosis Reveal a Common Immune-Evasion Strategy Used by Pathogenic and Commensal Bacteria. Immunity, 2015. 43(5): p. 909-22.
16. Needham, B. D, and M. S. Trent, Fortifying the barrier: the impact of lipid A remodeling on bacterial pathogenesis. Nat Rev Microbiol, 2013. 11(7): p. 467-81.
17. Alloatti, A., et al., Toll-like Receptor 4 Engagement on Dendritic Cells Restrains Phago-Lysosome Fusion and Promotes Cross-Presentation of Antigens. Immunity, 2015. 43(6): p. 1087-100.
18. Joffre, O. P., et al., Cross-presentation by dendritic cells. Nat Rev Immunol, 2012. 12(8): p. 557-69.
19. Horton, C., K. Shanmugarajah, and P. J. Fairchild, Harnessing the properties of dendritic cells in the pursuit of immunological tolerance. Biomed J, 2017. 40(2): p. 80-93.
20. Lutz, M. B, and C. Kurts, Induction of peripheral CD4+ T-cell tolerance and CD8+ T-cell cross-tolerance by dendritic cells. Eur J Immunol, 2009. 39(9): p. 2325-30.
21. Pulendran, B., Variegation of the immune response with dendritic cells and pathogen recognition receptors. J Immunol, 2005. 174(5): p. 2457-65.
22. Eke, P. I., et al., Prevalence of periodontitis in adults in the United States: 2009 and 2010. J Dent Res, 2012. 91(10): p. 914-20.
23. Pihlstrom, B. L., B. S. Michalowicz, and N. W. Johnson, Periodontal diseases. Lancet, 2005. 366(9499): p. 1809-20.
24. Abusleme, L., et al., The sub gingival microbiome in health and periodontitis and its relationship with community biomass and inflammation. ISME J, 2013. 7(5): p. 1016-25.
25. Haffajee, A. D., et al., Subgingival microbiota in healthy, well-maintained elder and periodontitis subjects. J Clin Periodontol, 1998. 25(5): p. 346-53.
26. Barth, K., D. G. Remick, and C. A. Genco, Disruption of immune regulation by microbial pathogens and resulting chronic inflammation. J Cell Physiol, 2013. 228(7): p. 1413-22.
27. Hajishengallis, G, and R. J. Lamont, Breaking bad: manipulation of the host response by *Porphyromonas gingivalis*. Eur J Immunol, 2014. 44(2): p. 328-38.
28. Coats. S. R., et al., Human Toll-like receptor 4 responses to *P. gingivalis* are regulated by lipid A 1- and 4'-phosphatase activities. Cell Microbiol, 2009. 11(11): p. 1587-99.
29. Kumada. H., et al., Structural study on the free lipid A isolated from lipopolysaccharide of *Porphyromonas gingivalis*. J Bacteriol, 1995. 177(8): p. 2098-106.
30. Curtis, M. A., et al., Temperature-dependent modulation of *Porphyromonas gingivalis* lipid A structure and interaction with the innate host defenses. Infect Immun, 2011. 79(3): p. 1187-93.
31. Li, H, and B. Shi, Tolerogenic dendritic cells and their applications in transplantation. Cell Mol Immunol, 2015. 12(1): p. 24-30.
32. Harding, C. V, and R. Song, Phagocytic processing of exogenous particulate antigens by macrophages for presentation by class I MHC molecules. J Immunol, 1994. 153(11): p. 4925-33.
33. Blander, J. M, and R. Medzhitov, Toll-dependent selection of microbial antigens for presentation by dendritic cells. Nature, 2006. 440(7085): p. 808-12.
34. Chen, T., et al., Identification and cloning of genes from *Porphyromonas gingivalis* after mutagenesis with a modified Tn4400 transposon from *Bacteroides fragilis*. Infect Immun, 2000. 68(1): p. 420-3.
35. Hirano, T., et al., Deep sequencing of *Porphyromonas gingivalis* and comparative transcriptome analysis of a LuxS mutant. Front Cell Infect Microbiol, 2012. 2: p. 79.
36. Genco, C. A., et al., Resistance of a Tn4351-generated polysaccharide mutant of *Porphyromonas gingivalis* to polymorphonuclear leukocyte killing. Infect Immun, 1995. 63(2): p. 393-401.
37. Genco, C. A., et al., Characterization of a Tn4351-generated hemin uptake mutant of *Porphyromonas gingivalis*: evidence for the coordinate regulation of virulence factors by hemin. Infect Immun, 1995. 63(7): p. 2459-66.
38. Njoroge, T., et al., A role for fimbriae in *Porphyromonas gingivalis* invasion of oral epithelial cells. Infect Immun, 1997. 65(5): p. 1980-4.
39. Wick, M. J., et al., Compartmentalization of defined epitopes expressed in *Escherichia coli* has only a minor influence on efficiency of phagocytic processing for pre- 39. sentation by class I and class II major histocompatibility complex molecules to T cells. Infect Immun. 1993. 61(11): p. 4848-56.
40. Global Burden of Disease Cancer, C., et al., Global, Regional, and National Cancer Incidence, Mortality, Years of Life Lost, Years Lived With Disability, and Disability-Adjusted Life-years for 32 Cancer Groups, 1990 to 2015: A Systematic Analysis for the Global Burden of Disease Study. JAMA Oncol, 2017. 3(4): p. 524-548.
41. Malhotra, J., S. K. Jabbour, and J. Aisner, Current state of immunotherapy for non-small cell lung cancer. Transl Lung Cancer Res, 2017. 6(2): p. 196-211.
42. Rodriguez-Cerdeira. C., et al., Advances in Immunotherapy for Melanoma: A Comprehensive Review. Mediators Inflamm, 2017. 2017: p. 3264217.
43. Farkona, S., E. P. Diamandis, and I. M. Blasutig, Cancer immunotherapy: the beginning of the end of cancer? BMC Med, 2016. 14: p. 73.
44. Fridman, W. H., et al., The immune contexture in human tumours: impact on clinical outcome. Nat Rev Cancer, 2012. 12(4): p. 298-306.
45. Zitvogel, L., et al., Mouse models in oncoimmunology. Nat Rev Cancer, 2016. 16(12): p. 759-773.
46. Leach, D. R., M. F. Krummel, and J. P. Allison, Enhancement of antitumor immunity by CTLA-4 blockade. Science, 1996. 271(5256): p. 1734-6.
47. Iwai, Y., S. Terawaki, and T. Honjo, PD-1 blockade inhibits hematogenous spread of poorly immunogenic tumor cells by enhanced recruitment of effector T cells. Int Immunol, 2005. 17(2): p. 133-44.
48. Vesely, M. D., et al., Natural innate and adaptive immunity to cancer. Annu Rev Immunol, 2011. 29: p. 235-71.
49. Shankaran, V., et al., IFNgamma and lymphocytes prevent primary tumour development and shape tumour immunogenicity. Nature, 2001. 410(6832): p. 1107-11.
50. Suggitt, M, and M. C. Bibby, 50 years of preclinical anticancer drug screening: empirical to target-driven approaches. Clin Cancer Res, 2005. 11(3): p. 971-81.
51. Schubert, S. M., et al., Ultra-sensitive protein detection via Single Molecule Arrays towards early stage cancer monitoring. Sci Rep, 2015. 5: p. 11034.
52. McCready, J., et al., Pregnancy-associated breast cancers are driven by differences in adipose stromal cells present during lactation. Breast Cancer Res. 2014. 16(1): p. R2.
53. Arendt, L. M., et al., Obesity promotes breast cancer by CCL2-mediated macrophage recruitment and angiogenesis. Cancer Res, 2013. 73(19): p. 6080-93.
54. Iyer, V., et al., Estrogen promotes ER-negative tumor growth and angiogenesis through mobilization of bone marrow-derived monocytes. Cancer Res, 2012. 72(11): p. 2705-13.
55. Keller, P. J., et al., Defining the cellular precursors to human breast cancer. Proc Natl Acad Sci USA, 2012. 109(8): p. 2772-7.
56. Proia, T. A., et al., Genetic predisposition directs breast cancer phenotype by dictating progenitor cell fate. Cell Stem Cell, 2011. 8(2): p. 149-63.
57. Jeselsohn, R., et al., Cyclin Dl kinase activity is required for the self-renewal of mammary stem and progenitor cells that are targets of MMTV-ErbB2 tumorigenesis. Cancer Cell, 2010. 17(1): p. 65-76.
58. DiMeo, T. A., et al., A novel lung metastasis signature links Wnt signaling with cancer cell self-renewal and epithelial-mesenchymal transition in basal-like breast cancer. Cancer Res, 2009. 69(13): p. 5364-73.
59. Wu, M., et al., Dissecting genetic requirements of human breast tumorigenesis in a tissue transgenic model of human breast cancer in mice. Proc Natl Acad Sci USA, 2009. 106(17): p. 7022-7.
60. Maroulakou, I. G., et al., Distinct roles of the three Akt isoforms in lactogenic differentiation and involution. J Cell Physiol, 2008. 217(2): p. 468-77.
61. Gupta, P. B., et al., Systemic stromal effects of estrogen promote the growth of estrogen receptor-negative cancers. Cancer Res, 2007. 67(5): p. 2062-71.
62. Proia, D. A, and C. Kuperwasser, Reconstruction of human mammary tissues in a mouse model. Nat Protoc, 2006. 1(1): p. 206-14.
63. Kuperwasser, C., et al., A mouse model of human breast cancer metastasis to human bone. Cancer Res, 2005. 65(14): p. 6130-8.
64. Kuperwasser, C., et al., Reconstruction of functionally normal and malignant human breast tissues in mice. Proc Nat Acad Sci USA, 2004. 101(14): p. 4966-71.
65. Kuperwasser, C., et al., Development of spontaneous mammary tumors in BALB/c p53 heterozygous mice. A model for Li-Fraumeni syndrome. Am J Pathol, 2000. 157(6): p. 2151-9.
66. Jerry, D. J., et al., A mammary-specific model demonstrates the role of the p53 tumor suppressor gene in tumor development. Oncogene, 2000. 19(8): p. 1052-8.
67. Jerry, D. J., et al., Delayed involution of the mammary epithelium in BALB/c-p53null mice. Oncogene, 1998. 17(18): p. 2305-12.
68. Goel, V. K., et al. Melanocytic nevus-like hyperplasia and melanoma in transgenic BRAFV600E mice. Oncogene, 2009. 28(23): p. 2289-98.
69. Luo, C., et al., Expression of oncogenic BRAFV600E in melanocytes induces Schwannian differentiation in vivo. Pigment Cell Melanoma Res, 2015. 28(5): p. 603-6.
70. Cao, J., et al., The E3 ligase APC/C(Cdh1) promotes ubiquitylation-mediated proteolysis of PAX3 to suppress melanocyte proliferation and melanoma growth. Sci Signal, 2015. 8(392): p. ra87.
71. Luo, C., et al., Loss of ARF sensitizes transgenic BRAFV600E mice to UV-induced melanoma via suppression of XPC. Cancer Res, 2013. 73(14): p. 4337-48.
72. Koya, R. C., et al., BRAF inhibitor vemurafenib improves the antitumor activity of adoptive cell immunotherapy. Cancer Res, 2012. 72(16): p. 3928-37.
73. Rashidian, M., et al., Predicting the response to CTLA-4 blockade by longitudinal noninvasive monitoring of CD8 T cells. J Exp Med, 2017. 214(8): p. 2243-2255.
74. Homet Moreno, B., et al., Combined treatment with dabrafenib and trametinib with immune-stimulating antibodies for BRAF mutant melanoma. Oncoimmunology, 2016. 5(7): p. e1052212.
75. Xu, L., et al., Rehmannia glutinosa polysaccharide induces toll-like receptor 4 dependent spleen dendritic cell maturation and anti-cancer immunity. Oncoimmunology, 2017. 6(7): p. e1325981.
76. Ligtenberg, M. A., et al., Cripto-1 vaccination elicits protective immunity against metastatic melanoma. Oncoimmunology, 2016. 5(5): p. e1128613.
77. Sugiura, K, and C. C. Stock, Studies in a tumor spectrum. I. Comparison of the action of methylbis (2-chloroethyl)amine and 3-bis(2-chloroethyl)aminomethyl-4-methoxymethyl-5-hydroxy-6-methylpyridine on the growth of a variety of mouse and rat tumors. Cancer, 1952. 5(2): p. 382-402.
78. Sirotnak, F. M., et al., New folate analogs of the 10-deaza-aminopterin series. Further evidence for markedly increased antitumor efficacy compared with methotrexate in ascitic and solid murine tumor models. Cancer Chemother Pharmacol, 1984. 12(1): p. 26-30.
79. Ott, P. A., et al., An immunogenic personal neoantigen vaccine for patients with melanoma. Nature, 2017. 547 (7662): p. 217-221.
80. El-Gabalawy, H., L. C. Guenther, and C. N. Bernstein, Epidemiology of immune-mediated inflammatory diseases: incidence, prevalence, natural history, and comorbidities. J Rheumatol Suppl, 2010. 85: p. 2-10.
81. Zuber, J, and M. Sykes, Mechanisms of Mixed Chimerism-Based Transplant Tolerance. Trends Immunol, 2017.
82. Billingham, R. E., L. Brent, and P. B. Medawar, Actively acquired tolerance of foreign cells. Nature, 1953. 172 (4379): p. 603-6.
83. Crepeau, R. L, and M. L. Ford, Challenges and opportunities in targeting the CD28/CTLA-4 pathway in transplantation and autoimmunity. Expert Opin Biol Ther, 2017. 17(8): p. 1001-1012.
84. Ehst, B. D., E. Ingulli, and M. K. Jenkins, Development of a novel transgenic mouse for the study of interactions between CD4 and CD8 T cells during graft rejection. Am J Transplant, 2003. 3(11): p. 1355-62.
85. Reddy, A. T., S. P. Lakshmi, and R. C. Reddy, Murine model of allergen induced asthma. J Vis Exp, 2012(63): p. e3771.
86. Kianmehr, M., et al., The Effect of *Zataria multiflora* on Th1/Th2 and Th17/T Regulatory in a Mouse Model of Allergic Asthma. Front Pharmacol, 2017. 8: p. 458.
87. Mendel, I., N. Kerlero de Rosbo, and A. Ben-Nun, A myelin oligodendrocyte glycoprotein peptide induces typical chronic experimental autoimmune encephalomyelitis in H-2b mice: fine specificity and T cell receptor V beta expression of encephalitogenic T cells. Eur I immunol. 1995. 25(7): p. 1951-9.
88. Rangachari, M, and V. K. Kuchroo, Using EAE to better understand principles of immune function and autoimmune pathology. J Autoimmun, 2013. 45: p. 31-9.

What is claimed is:

1. A pharmaceutical composition comprising
a) a heat killed *Porphyromonas gingivalis* bacterium expressing a homogenous lipid A structure having a molecular negative mass ion of 1368, 1435/1449, or 1690/1768; and
b) a pharmaceutically acceptable carrier.

2. The composition of claim 1, further comprising an antigen.

3. The composition of claim 2, wherein the *P. gingivalis* bacterium expresses the antigen.

4. The composition of claim 2, wherein the antigen is absorbed to the *P. gingivalis* bacterium.

5. The composition of claim 2, wherein the antigen is selected from the group consisting of a tumor antigen, a bacterial antigen, a viral antigen, infectious disease antigens, and self-antigens.

6. The composition of claim 1, further comprising an adjuvant.

7. The composition of claim 6, wherein the adjuvant is selected from the group consisting of alum, incomplete Freund's adjuvant, montanide, GM-CSF, imiquimod, resiquimod, and a saponin.

8. An immunomodulatory agent comprising a heat killed *Porphyromonas gingivalis* bacterium expressing a homogenous lipid A structure having a molecular negative mass ion of 1368, 1435/1449, or 1690/1768.

9. A pharmaceutical composition comprising
a) a purified *P. gingivalis* lipopolysaccharide (LPS) where a lipid portion of LPS has a molecular negative mass ion of 1368, wherein the *P. gingivalis* bacterium is heat killed; and
b) a pharmaceutically acceptable carrier.

10. A method for stimulating an immune response in a subject comprising administering a composition comprising a heat killed *Porphyromonas gingivalis* bacterium expressing a homogenous lipid A structure having a molecular negative mass ion of 1368, 1435/1449, or 1690/1768 and an antigen, wherein the composition promotes an immune response to the antigen.

11. The method of claim 10, wherein the composition elicits a T cell response to the antigen.

12. The method of claim 10, wherein the composition is administered for treatment of a tumor.

13. The method of claim 10, wherein the composition is administered for treatment of cancer.

14. The method of claim 10, wherein the antigen is a tumor antigen.

15. The method of claim 10, wherein the antigen is an infectious disease antigen.

16. The method of claim 10, wherein the composition comprises at least two different antigens.

17. The method of claim 10, wherein the composition further comprises an adjuvant.

18. A method for suppressing an immune response in a subject comprising administering a composition comprising a heat killed *Porphyromonas gingivalis* bacterium expressing a homogenous lipid A structure having a molecular negative mass ion of 1368, 1435/1449, or 1690/1768 and an antigen, wherein the composition inhibits an immune response to the antigen.

19. The method of claim 18, wherein the inhibition of an immune response comprises inducing tolerance to the antigen.

20. The method of claim 18, wherein the inhibition of an immune response comprises suppressing an immune response to the antigen.

21. The method of claim 18, wherein the composition induces dendritic cells to express immune-regulatory modulators.

22. The method of claim 21, wherein the immune-regulatory modulators comprise co-inhibitory ligands or immune suppressive cytokines.

23. The method of claim 18, wherein the composition is administered for treatment of an autoimmune disease or disorder.

24. The method of claim 18, wherein the composition is administered for treatment of an allergy.

25. The method of claim 18, wherein the composition is administered for treatment of graft versus host disease.

26. The method of claim 18, wherein the antigen is a self-antigen.

27. The method of claim 18, wherein the composition further comprises an adjuvant.

28. A method stimulating an immune response against a tumor in a subject, comprising administering to the subject a composition comprising a heat killed *Porphyromonas gingivalis* bacterium expressing a homogenous lipid A structure having a molecular negative mass ion of 1368, 1435/1449, or 1690/1768 and a tumor antigen from the tumor, in an amount sufficient to elicit an immune response against the tumor in the subject.

29. A method for suppressing an immune response against a self-antigen in a subject suffering from an autoimmune disease, comprising administering to the subject a composition comprising a heat killed *Porphyromonas gingivalis* bacterium expressing a homogenous lipid A structure having a molecular negative mass ion of 1368, 1435/1449, or 1690/1768 and a self-antigen, in an amount sufficient to suppress the immune response against the self-antigen.

30. A method of treating cancer, infectious disease, or autoimmunity in a subject comprising administering the composition of claim 1.

* * * * *